United States Patent [19]
Baekkeskov et al.

[11] Patent Number: 5,998,584
[45] Date of Patent: *Dec. 7, 1999

[54] REAGENTS AND METHODS FOR THE DIAGNOSIS AND TREATMENT OF DIABETES AND STIFF MAN SYNDROME

[75] Inventors: Steinunn Baekkeskov, San Francisco, Calif.; Wiltrud Richter, Ulm, Germany; Yuguang Shi; Mark Namchuk, both of San Francisco, Calif.; John Kim, Berkeley, Calif.

[73] Assignee: Reagents of the University of California, Oakland, Calif.

[ * ] Notice: This patent is subject to a terminal disclaimer.

[21] Appl. No.: 08/949,017

[22] Filed: Oct. 10, 1997

Related U.S. Application Data

[60] Continuation of application No. 08/450,755, May 25, 1995, Pat. No. 5,849,506, which is a division of application No. 08/161,290, Dec. 2, 1993, Pat. No. 5,691,448, which is a continuation-in-part of application No. 07/984,935, Dec. 3, 1992, abandoned.

[51] Int. Cl.⁶ .................................................. C07K 14/47
[52] U.S. Cl. ........................ 530/350; 435/69.3; 435/70.3; 436/506; 436/811
[58] Field of Search ...................... 530/350, 324, 530/326; 435/7.4, 69.3, 70.3; 436/506, 811

[56] References Cited

U.S. PATENT DOCUMENTS 5,674,978 10/1997 Tobin et al. ............................. 530/326
5,691,448 11/1997 Baekkeskov et al. .................. 530/350

*Primary Examiner*—Donna C. Wortman
*Attorney, Agent, or Firm*—Townsend & Townsend & Crew

[57] ABSTRACT

The invention provides fragments of $GAD_{65}$ that are specifically reactive with at least one class of $GAD_{65}$ autoantibody. Most fragments are substantially free of N-terminal amino acids that would otherwise limit solubility. Different fragment contain epitopes for different classes of $GAD_{65}$ autoantibodies. The fragments are used in methods of diagnosing and treating insulin dependent diabetes mellitus and stiff man syndrome.

8 Claims, 12 Drawing Sheets

```
hGAD65  MASPGSGFWSFGSEDGSGDSENPGTARAWCQVAQKFTGGIGNKLCALLYGDAEKPAESGG  60
rGAD65                           P                          S

SQPPRAAARKAACACDQKPCSCSKVDVNYAFLHATDLLPACDGERPTLAFLQDVMNILLQ  120
           VTS       T   PG                   E

YVVKSFDRSTKVIDFHYPNELLQEYNWELADQPQNLEEILMHCQTTLKYAIKTGHPRYFN  180
                                              T

QLSTGLDMVGLAADWLTSTANTNMFTYEIAPVFVLLEYVTLKKMREIIGWPGGSGDGIFS  240
                                      V

PGGAISNMYAMMIARFKMFPEVKEKGMAALPRLIAFTSEHSHFSLKKGAAALGIGTDSVI  300
                       L Y                V

LIKCDERGKMIPSDLERRILEAKQKGFVPFLVSATAGTTVYGAFDPLLAVADICKKYKIW  360
                                 V

MHVDAAWGGGLLMSRKHKWKLSGVERANSVTWNPHKMMGVPLQCSALLVREEGLMQNCNQ  420
                       N                                        S

MHASYLFQQDKHYDLSYDTGDKALQCGRHVDVFKLWLMWRAKGTTGFEAHVDKCLELAEY  480
                                                              I

LYNIIKNREGYEMVFDGKPQHTNVCFWYIPPSLRTLEDNEERMSRLSKVAPVIKARMMEY  540
                                 FV                     V

FIG. 1. GTTMVSYQPLGDKVNFFRMVISNPAATHQDIDFLIEEIERLGQDL  585
```

5,998,584

REAGENTS AND METHODS FOR THE DIAGNOSIS AND TREATMENT OF DIABETES AND STIFF MAN SYNDROME

CROSS-REFERENCE TO RELATED APPLICATIONS

This is a Continuation U.S. Ser. No. 08/450,755, filed May 25, 1995, now U.S. Pat. No. 5,849,506, which is a division of U.S. Ser. No. 08/161,290 filed Dec. 2, 1993, now U.S. Pat. No. 5,691,448, which is a continuation-in-part of Ser. No. 07/984,935, filed Dec. 3, 1992, abandoned, which are incorporated by reference in their entirety for all purposes.

STATEMENT OF GOVERNMENT INTEREST

This invention was supported by grants from the National Institutes of Health (#1P01 DK41822-01) and the March of Dimes (6-FY93-0695). The government may have certain rights in this invention.

TECHNICAL FIELD

The present invention relates generally to improved reagents and methods for identifying and treating individuals who suffer from, or are susceptible to, insulin dependent diabetes mellitus or stiff man syndrome.

BACKGROUND ART

Insulin-dependent diabetes mellitus (IDDM) (also known as type 1 diabetes) primarily afflicts young people. Although insulin is available for treatment, the several-fold increased morbidity and mortality associated with this disease require the development of early diagnostic and preventive methods. The destruction of pancreatic β-cells (which are the insulin-secreting cells of the islets of Langerhans) that precedes the clinical onset of IDDM, is mediated by autoimmune mechanisms. Among the most thoroughly studied autoimmune abnormalities associated with the disease is the high incidence of circulating β-cell specific autoantibodies at the time of diagnosis. Family studies have shown that the autoantibodies appear prior to overt IDDM by a number of years, suggesting a long prodromal period of humoral autoimmunity before clinical symptoms emerge. The family studies have also documented a slow, progressive loss of insulin response to intravenous glucose in the years preceding diagnosis. The presence of β-cell specific autoantibodies in the prediabetic period is likely to reflect the ongoihg autoimmune process, one that eventually leads to critical β-cell depletion and insulin dependency. It has been estimated that only 10% of the total β-cell mass remains at the time of clinical onset.

The target of autoantibodies in pancreatic β-cells in IDDM was originally identified as a 64 kDa autoantigen by immunoprecipitation experiments using detergent lysates of human islets (Baekkeskov et al. (1982), *Nature* 298:167–169). Antibodies to the 64 kDa autoantigen precede the clinical onset of IDDM and have been shown to have an incidence of about 80% at clinical onset and during the prediabetic period (Baekkeskov et al. (1987), *J. Clin. Invest.* 79:926–934; Atkinson et al. (1990), *Lancet* 335:1357–1360; and Christie et al. (1988), *Diabetologia* 31:597–602) (each of which is incorporated by reference in its entirety for all purposes). The rat and human 64 kDa protein are highly homologous with regard to autoantigenic epitopes (Christie et al. (1990),*J. Boil. Chem.* 265:376–381) (incorporated by reference in its entirety for all purposes).

The 64 kDa autoantigen in islets of Langerhans is detected in three different forms with regard to hydrophobicity and compartmentalization: a hydrophilic soluble form of 65 kDa and Pi of approximately 7.1; a 64 kDa hydrophobic form, which is soluble or of a low membrane avidity and has a Pi of approximately 6.7; and a hydrophobic firmly membrane anchored form of the same electrophoretic mobility and Pi. Both the membrane bound and the soluble hydrophobic 64 kDa forms exist as two isoforms, α and β which have identical Pi and hydrophobic properties but differ by approximately 1 kDa (Baekkeskov et al. (1989), *Diabetes* 38:1133–1141) (incorporated by reference in its entirety for all purposes). The 64 kDa autoantigen was found to be β-cell specific in an analysis of a number of tissues, which did not include the brain (Christie et al., supra).

It has recently been shown that the 64 kDa autoantigen of pancreatic β-cells is glutamic acid decarboxylase (GAD, L-glutamate 1-carboxy-lyase, EC 4.1.1.15). The GAD enzyme synthesizes GABA from glutamic acid and is an abundant protein of GABA-secreting neurons in the central nervous system (CNS). See copending application, Ser. No. 07/756,207; Baekkeskov et al. (1990), *Nature* 347:151–157 (incorporated by reference in its entirety for all purposes).

GAD is an abundant and partially-characterized protein of GABA-secreting neurons in the central nervous system. The GAD enzyme has two forms encoded by two distinct non-allelic genes, $GAD_{67}$ and $GAD_{65}$ (also known as GAD-1 and GAD-2), which may have developed from a common ancestral gene during vertebrate phylogeny. $GAD_{67}$ and $GAD_{65}$ are highly diverse in the first 95 amino acids but share significant (approx. 75%) homology in the rest of the molecule. Both have a proteolytic hot spot 80–90 amino acids from the N-terminus (Christgau et al. (1991),*J. Boil. Chem.* 266:21257–21264; Christgau et al. (1992), *J. Cell Biol.* 118:309–320) (incorporated by reference in their entirety for all purposes), which may represent a domain boundary. The N-terminal domain harbors the post-translational modifications which result in anchoring of $GAD_{65}$ to the membrane of synaptic vesicles and control the distinct subcellular localization of this protein.

In brain tissue, both $GAD_{65}$ and $GAD_{67}$ are produced (Bu et al. (1992), *Proc. Natl. Acad. Sci. USA* 89:2115–2119; Kaufman et al. (1986), Science 232:1138–1140; Chang & Gottlieb (1988), *J. Neurosci.* 8:2123–2130) (each of which is incorporated by reference in its entirety for all purposes). Some species express both GAD proteins in their pancreatic islets. However, in human islets only $GAD_{65}$ is expressed (Karlsen et al. (1991), *Proc. Natl. Acad. Sci. (USA)* 88:8337–8341; Karlsen et al. (1992), *Diabetes* 41:1355–1359) (incorporated by reference in their entirety for all purposes). Immunogenic crossreactivity between isolates of $GAD_{65}$ and $GAD_{67}$ from different vertebrate species indicates a high degree of conservation of antigenic determinants from rodents to humans (Legay et al. (1986), *J. Neurochem.* 46:1478–1486). Consistent with this observation, human $GAD_{65}$ and $GAD_{67}$ polypeptides share more than 90% amino-acid sequence identity with cognate polypeptides in other mammals. Bu et al., supra.

The cDNAs of human CNS $GAD_{67}$ and $GAD_{65}$ have been cloned and sequenced (Bu et al., supra). Karlsen et al. (1991), supra, have reported sequence data for human pancreatic beta cell $GAD_{65}$. DNA sequence information is also available for rat CNS $GAD_{65}$ and $GAD_{67}$ (Erlander et al. (1991), *Neuron* 7:91–100; Julien et al. (1990), *J. Neurochem.* 54:703–705) and rat beta cell $GAD_{65}$ (Michelson et al. (1991), *Proc. Natl. Acad. Sci. (USA)* 88:8754–8758) (each of which is incorporated by reference in its entirety for all purposes).

The demonstrated equivalence of the 64 kDa IDDM autoantigen and GAD explains earlier observations linking IDDM with a rare, but severe, neurological disease termed stiff man syndrome, in which GAD has been recognized as the predominant autoantigen (Solimena et al. (1988), *N. Engl. J. Med.* 318:1012–1020; Solimena et al. (1990), *N. Engl. J. Med.* 322:1555–1560) (incorporated by reference in their entirety for all purposes). Almost all the GABA-ergic neuron autoantibody positive patients were also positive for islet cell cytoplasmic antibodies, and one third had IDDM. In addition, autoantibodies to GABA-ergic neurons were detected in 3 of 74 IDDM patients without SMS (Solimena et al. (1988), supra, and Solimena et al. (1990), supra). Other studies have also reported a high incidence of IDDM in SMS patients (Lorish et al. (1989), *Mayo Clin. Proc.* 64:629–636).

The demonstrated equivalence of the 64 kDa antigen and GAD has also led to some improvement in methods of diagnosing IDDM. Previously, the 64 kDa autoantigen had only been identified in the pancreatic β-cell, and could not be purified in sufficient quantities to allow cloning, sequencing or other characterization that would have permitted large-scale preparation of reagents necessary for efficient detection or therapy. By contrast, the abundance of GAD in brain allows facile production by cloning, or otherwise, of large amounts of GAD protein (either $GAD_{65}$ or $GAD_{67}$) as a reagent for diagnosis. See co-pending application Ser. No. 07/756,207.

Although an improvement on prior methods, diagnosis using full-length forms of purified GAD protein is still not entirely satisfactory. GAD molecules have a lipid modification in the N-terminal region and are therefore insoluble except in the presence of detergent. The insolubility of full-length GAD molecules hampers purification, and use of GAD, in simple assays like immunoprecipitation, ELISA or radioimmunoassay. Moreover, use of full-length GAD as a diagnostic reagent does not distinguish between different classes of GAD autoantibodies, which may be diagnostic of different temporal stages of an autoimmune disease and/or different diseases. Furthermore, insoluble GAD proteins are unsuitable for in vivo administration as therapeutic reagents.

Based on the foregoing, it is apparent that a need exists for improved reagents and methods for diagnosing and treating patients having, or at risk of, IDDM and stiff man syndrome. The present invention fulfills this and other needs.

SUMMARY OF THE INVENTION

According to one embodiment of the invention, soluble fragments of $GAD_{65}$ protein are provided. The fragments are specifically reactive with at least one class of $GAD_{65}$ autoantibody. The fragments are usually substantially free of N-terminal amino acids that would otherwise limit solubility. In some fragments, the N-terminal amino acids 24–31 and preferably 45 of a $GAD_{65}$ protein are deleted or mutated. Other fragments contain a larger deletion of N-terminal sequences, which can cover amino acids 1–244. Some fragments are also substantially free of a segment having an epitope specifically reactive with a $GAD_{65}$ autoantibody. These fragments are useful for methods of differential diagnosis (e.g., distinguishing IDDM from stiff man syndrome or distinguishing different temporal stages of IDDM). For example, in some fragments, the segment covering amino acids 545–585 is removed, in other fragments, the segment from amino acids 245–295.

Some soluble fragments comprise a contiguous sequence from about amino acids 245–585 of a $GAD_{65}$ protein. These fragments are specifically reactive with three different classes of autoantibodies against the $GAD_{65}$ protein that are diagnostic of IDDM.

Other soluble fragments comprise a contiguous sequence of at least eight amino acids from amino acids 1–20 or 70–101. These fragments are specifically reactive with two classes of autoantibodies against the $GAD_{65}$ protein that are diagnostic of stiff man syndrome. Some of these fragments are substantially free of amino acids 245–585 and are thereby rendered incapable of specific binding to three classes of autoantibodies diagnostic of IDDM.

In another aspect of the invention, methods for detecting $GAD_{65}$ autoantibodies in serum are provided. In some methods, a soluble fragment of $GAD_{65}$ is used as the diagnostic reagent. In these methods, a serum sample is exposed to a soluble $GAD_{65}$ fragment, and a specific interaction between the $GAD_{65}$ fragment and a $GAD_{65}$ autoantibody is detected.

In other methods, a fusion polypeptide having two components is provided as a diagnostic reagent. The two components are a $GAD_{65}$ protein, or a fragment thereof that is specifically reactive with a $GAD_{65}$ autoantibody, and an extension peptide fused to the N-terminal of the protein or fragment. The fusion polypeptide is immobilized to a solid support via the extension peptide and exposed to a serum sample. Attachment via the extension peptide ensures that $GAD_{65}$ autoantibody-binding epitopes in the $GAD_{65}$ protein or fragment thereof are accessible to bind autoantibodies. Specific interaction between the $GAD_{65}$ protein or fragment and $GAD_{65}$ autoantibodies in the serum is detected.

In other methods, a $GAD_{65}$ protein or fragment thereof is immobilized to a solid support via an antibody specifically reactive with a first epitope occurring within amino acids 1–244 of a $GAD_{65}$ protein or fragment thereof. Immobilization via the antibody leaves the remainder of the $GAD_{65}$ protein or fragment, which contains a second epitope specifically reactive with a $GAD_{65}$ autoantibody, accessible for binding to autoantibodies. Specific interaction between the $GAD_{65}$ protein or fragment and $GAD_{65}$ autoantibodies in the serum is detected.

In another aspect of the invention, methods of differential diagnosis are provided. These methods distinguish different temporal stages of an IDDM, and/or distinguish IDDM from stiff man syndrome. To distinguish SMS and IDDM, serum is exposed to a $GAD_{65}$ fragment having an epitope specifically reactive with a $GAD_{65}$ autoantibody diagnostic of stiff man syndrome and free of segments specifically reactive with autoantibodies diagnostic of IDDM. For example, fragments consisting essentially of amino acids 1–20, 70–101 and 1–101 are suitable. In other methods, a serum sample is exposed to different $GAD_{65}$. fragments possessing epitopes reactive with different classes of $GAD_{65}$ autoantibodies. Often the different classes of autoantibodies are diagnostic of different temporal stages of IDDM.

In another aspect of the invention, methods of treating IDDM or stiff man syndrome are provided. In some methods, a therapeutically effective dosage of a soluble $GAD_{65}$ fragment that is specifically reactive with a $GAD_{65}$ autoantibody or T-cell is administered to a patient to induce immunotolerance to a $GAD_{65}$ autoantigen. In another method, a soluble $GAD_{65}$ fragment is used to generate T-helper cells specific for the $GAD_{65}$ fragment from peripheral blood cells obtained from a patient. The T-helper cells so generated, or a portion thereof, which is capable of including an in vivo immune response against the T-helper cells, is administered to the patient.

BRIEF DESCRIPTION OF THE DRAWINGS

FIG. 1 shows the amino acid sequences of human (upper) and rat (lower) $GAD_{65}$ proteins. For the rat sequence, only amino acids that differ from the human sequence are shown.

6A. Summary of antibody binding to rat $GAD_{65}$ mutants expressed in COS-7 cells. GAD1 and GAD6 are mouse anti-GAD monoclonal antibodies (Gottlieb et al., 1986, Chang and Gottlieb 1988). GAD1 is distinct from other monoclonals in only recognizing intact $GAD_{65}$. GAD6 has a recognition pattern similar to MICA2, except that GAD6 reacts equally well in native and denatured conditions.

6B. Immunoprecipitation of N-terminal deletion mutants of rat $GAD_{65}$ expressed in COS-7 cells with MICAS, GAD6 and human IgG (control).

6C. Immunoprecipitation of C-terminal deletion mutants of rat $GAD_{65}$ expressed in COS-7 cells with MICAS, GAD6 and human IgG (control).

Figure 7:
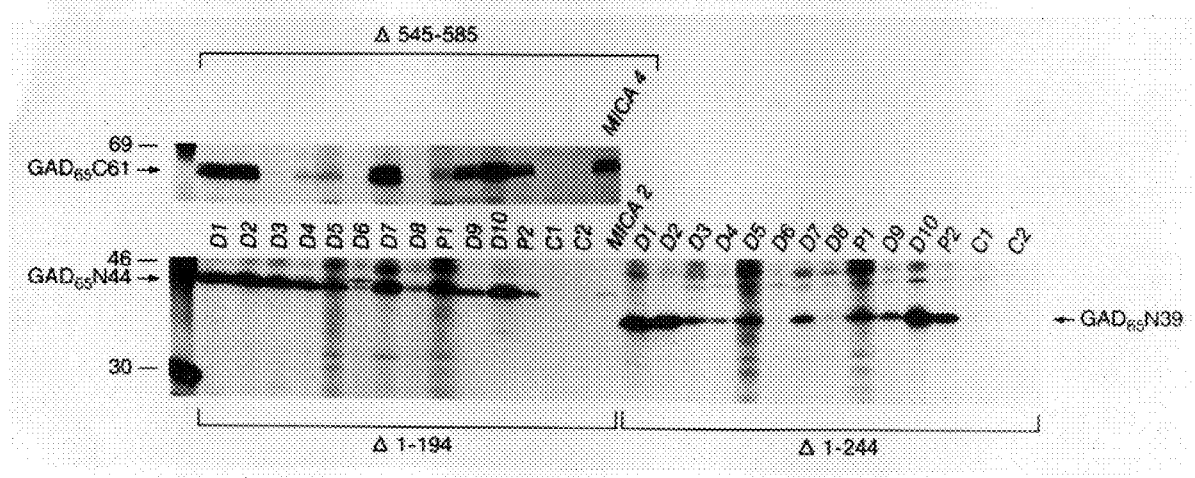

FIG. 7 shows immunoprecipitation of N-terminal and C-terminal deletion mutants of rat $GAD_{65}$ expressed in COS-7 cells with sera from nine independent newly diagnosed diabetic patients (D1–9). Sera from a prediabetic individual (PI), an individual positive for islet cell cytoplasmic antibodies (P2), and two healthy control individuals (C1 and C2), were also analyzed. The D10 serum is from the patient from whom MICAs 1–6 were derived.

Figure 8:
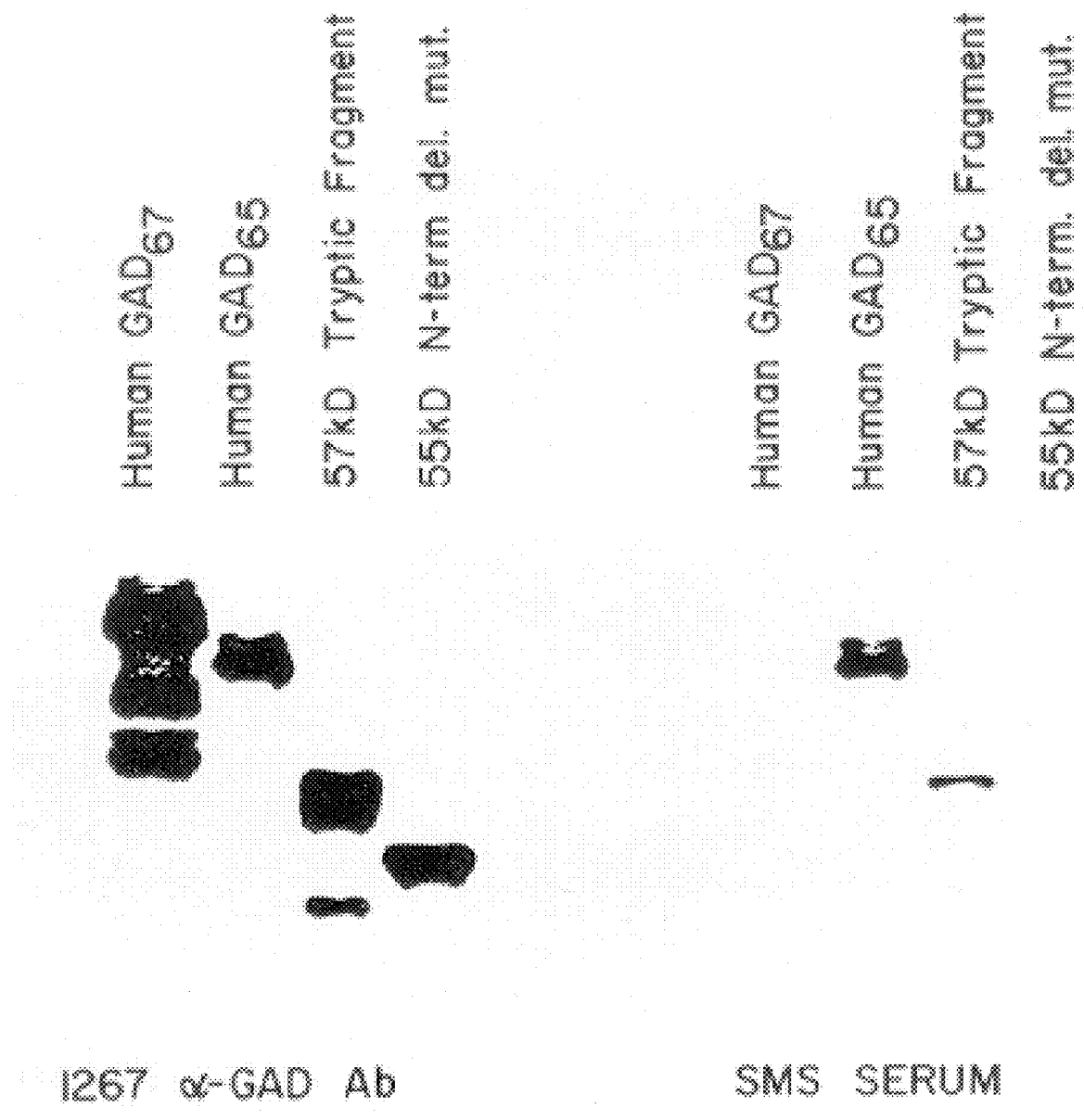

FIG. 8 shows Western blotting of $GAD_{67}$, $GAD_{65}$, $GAD_{65}$ Δ1–69/70, and $GAD_{65}$ Δ1–101, stained with a typical SMS serum, and a positive control serum.

Figure 9:
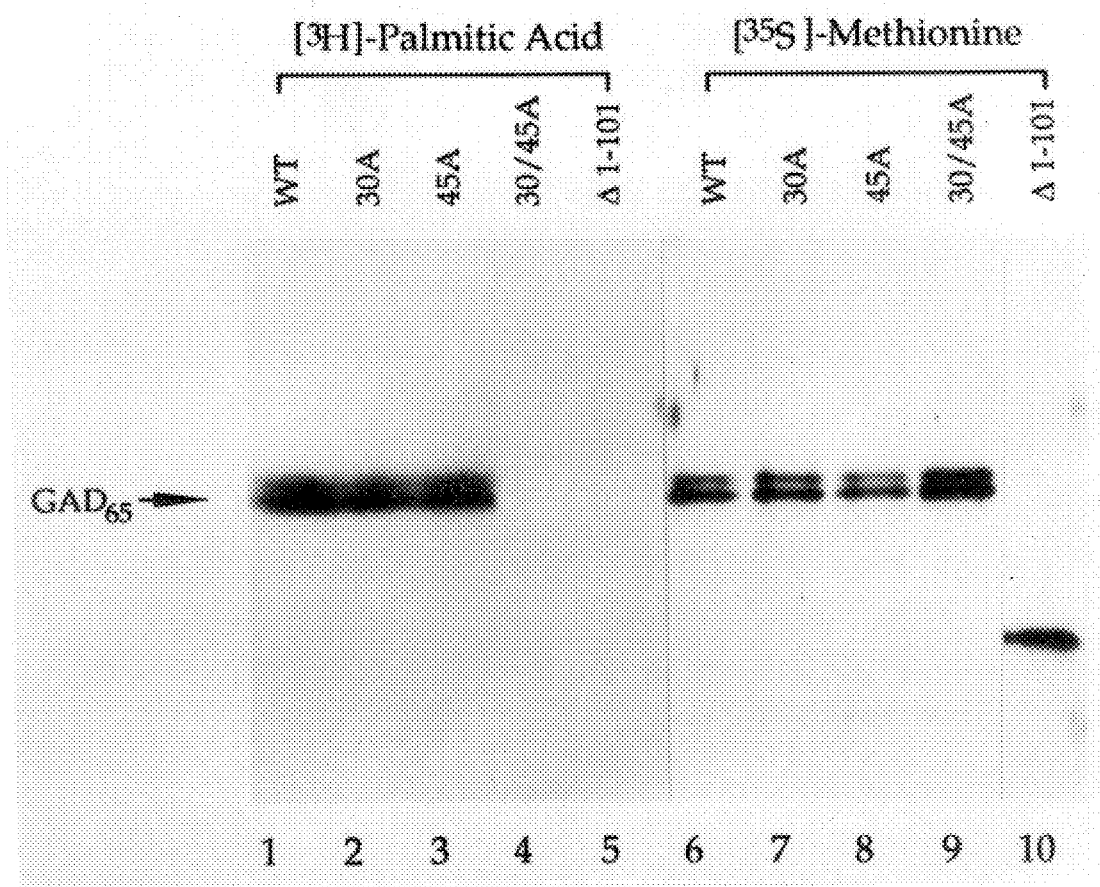

FIG. 9 shows SDS gel analysis of $GAD_{65}$ and mutant proteins labeled by [$^3$H]-palmitic acid and [$^{35}$S]-methionine.

Figure 10:
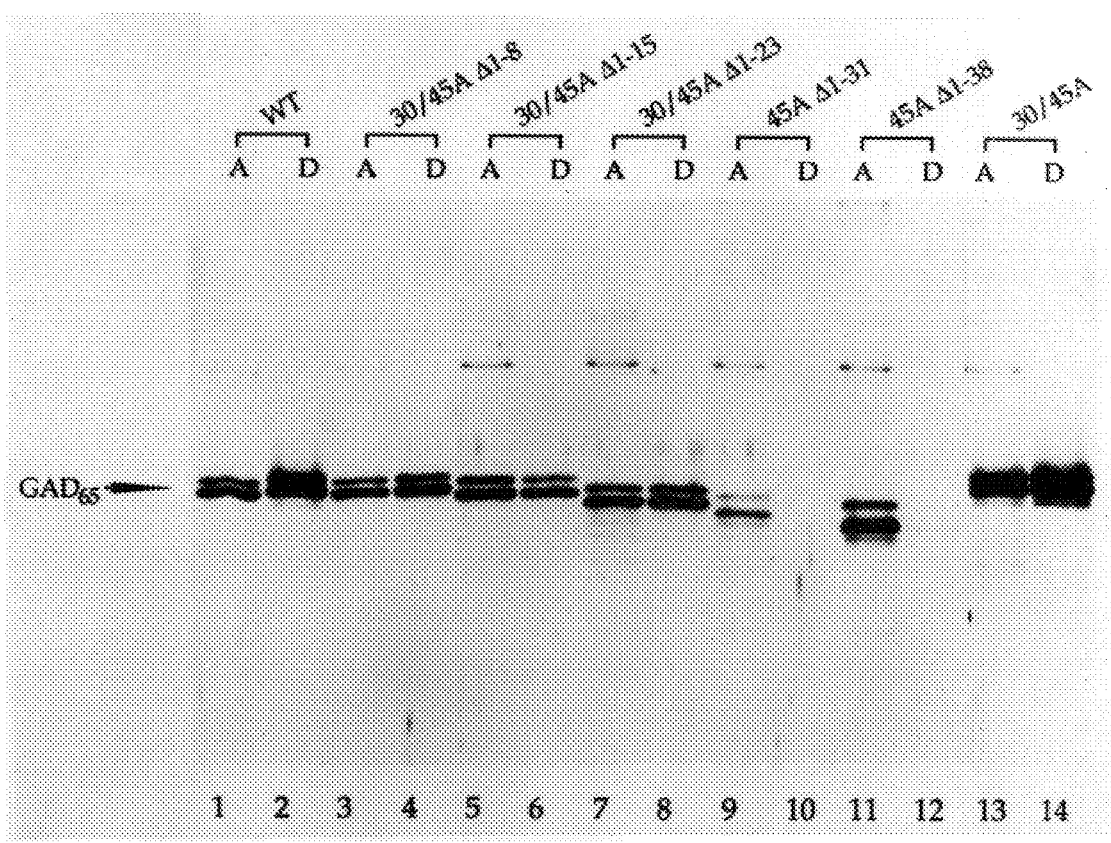

FIG. 10 shows Western blotting of aqueous (A) and detergent (D) fractions of total cellular protein from COS cells expressing $GAD_{65}$ and N-terminal deletion mutants, stained with sera reactive with a $GAD_{65}$ C-terminal peptide.

DEFINITIONS

When a $GAD_{65}$ fragment is described as "substantially free" of a segment of amino acids, at least about 50%, more usually at least about 75%, and most commonly at least about 90% of the amino acids within the specified segment are absent or substituted. The removal of these amino acids confers a change in a biological or chemical property of the residual fragment, such as the loss of capacity to react with a class of autoantibody, or the acquisition of solubility in aqueous solvents.

The terms "specific interaction" and "specifically reactive" mean that the dissociation constant for binding of a ligand and antibody is usually less than about 1 μM, more usually less than about 10 nM and sometimes less than about 1 nM.

The term "cognate" refers to a gene sequence that is evolutionarily and functionally related between species. For example, in the human genome, the human CD4 gene is the cognate gene to the mouse CD4 gene, since the sequences and structures of these two genes indicate that they are highly homologous and both genes encode a protein which functions in signaling T cell activation through MHC class II-restricted antigen recognition. Preferred cognate genes are: human, rat, rabbit, canine, nonhuman primate, porcine, murine and hamster.

The term $GAD_{65}$ analog includes any protein that competes with the rat $GAD_{65}$ protein of Bu et al. (1992), *Proc. Natl. Acad. Sci. (USA)* 89:2115–2119, for binding to $GAD_{65}$ autoantibodies. Analogs include natural and induced mutant polypeptides. Analog proteins may include stereoisomers (i.e., D-amino acids) of the twenty conventional amino acids, unnatural amino acids such as α,α-disubstituted amino acids, N-alkyl amino acids, lactic acid, 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, ω-N-methylarginine, and other similar amino acids and imino acids (e.g., 4-hydroxyproline). Analog proteins also include proteins having backbones modified by phosphorylation, glycosylation, palmitoylation and the like.

Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60° C. As other factors may significantly affect the stringency of hybridization, including, among others, base composition and size of the complementary strands, the presence of organic solvents and the extent of base mismatching, the combination of parameters is more important than the absolute measure of any one.

The term "substantially soluble" means that a fragment typically exhibits a solubility of at least 50 μg/ml and usually at least 100 μg/ml in an aqueous solvent.

The term "polypeptide" refers to a polymer of amino acids and includes full-length proteins and fragments thereof.

DESCRIPTION OF THE SPECIFIC EMBODIMENTS

I. Reagents for Diagnosis of IDDM and Stiff Man Syndrome

According to one embodiment of the invention reagents for diagnosis of patients suffering from, or at risk of IDDM and/or stiff man syndrome are provided. The polypeptides are usually soluble $GAD_{65}$ fragments that bind one or more $GAD_{65}$ autoantibodies diagnostic for one of these diseases.

A. Autoantibodies to $GAD_{65}$

As discussed supra, $GAD_{65}$ is one of two genes (the other being $GAD_{67}$) that encode two subtypes of the GAD enzyme. Within each nonallelic subtype there also exist several allelic variants (see Background Section). Thus, the term $GAD_{65}$ autoantibody includes autoantibodies reactive with any allelic variant of the $GAD_{65}$ enzyme or an epitope thereof. For example, the term $GAD_{65}$ autoantibody encompasses autoantibodies to the 64 kDa pancreatic β-cell autoantigen. Detection of autoantibodies to $GAD_{65}$ in human serum is diagnostic of IDDM and/or stiff man syndrome. Detection of autoantibodies to $GAD_{67}$ may also be a feasible method of diagnosis. However, the results of Example 3 suggests that autoantibodies to $GAD_{65}$ enzyme are much more prevalent than those to $GAD_{67}$. Thus, detection of autoantibodies to $GAD_{65}$ is preferred.

B. Production of $GAD_{65}$ Polypeptides

Frequently, autoantibodies to $GAD_{65}$ enzyme are detected using fragments of $GAD_{65}$ polypeptides. These fragments are produced by a variety of methods. The fragments of the present invention may be natural, i.e., fragments of CNS or pancreatic $GAD_{65}$, isolated from suitable sources, such as human or non-human CNS and pancreatic cells. Methods for such isolation are described in Oertel et al. (1980), *Brain Res. Bull.* Vol. 5, Suppl. 2, pp 713–719; Oertel et al. (1981), *J. Neurosci.* 6:2689–2700; and Chang & Gottlieb (1988), *J. Neurosci.* 8:2123–2130 (each of which is incorporated by reference in its entirety for all purposes). Usually, natural polypeptides will be isolated from CNS cells where $GAD_{65}$ is more abundant than in pancreatic cells. Purified compositions from the pancreatic form of $GAD_{65}$ can be isolated and characterized fully using CNS GAD65 as a reference. Because $GAD_{65}$ genes and proteins are highly conserved among species, the $GAD_{65}$ protein and fragments thereof utilized in the present invention can be human or nonhuman.

Natural polypeptides are isolated by conventional techniques such as affinity chromatography. For example, polyclonal or monoclonal antibodies are raised against previously-purified $GAD_{65}$ and attached to a suitable affinity column by well known techniques. See, e.g., Hudson & Hay, *Practical Immunology* (Blackwell Scientific Publications, Oxford, United Kingdom, 1980), Chapter 8 (incorporated by reference in its entirety for all purposes). Usually, an intact form of $GAD_{65}$ is obtained by such isolation techniques. Peptide fragments are generated from intact $GAD_{65}$ by chemical or enzymatic cleavage of the intact molecule.

As an alternative to isolating intact $GAD_{65}$ protein and fragments thereof from natural sources, these polypeptides are prepared based on the nucleotide sequence of a $GAD_{65}$ gene or amino acid sequence of a GAD protein. Extensive $GAD_{65}$ nucleic acid and amino acid sequence data from various species is already available. (See Background Section). Additional data, if required, are readily generated by conventional methods. For example, a known nucleotide sequence from one species can be used as a probe to clone $GAD_{65}$ genes from other species. Alternatively, antibodies to a known $GAD_{65}$ protein can be used as probes to detect $GAD_{65}$ expression products. Once cloned, $GAD_{65}$ genes are readily sequenced by conventional methods.

Synthetic proteins and polypeptides can be produced by at least three general approaches. First, polypeptides having up to about 150 amino acids, usually having fewer than about 100 amino acids, and more usually having fewer than about 75 amino acids, may be synthesized by the well known Merrifield solid-phase synthesis method in which amino acids are sequentially added to a growing chain. See Merrifield (1963), *J. Am. Chem. Soc.* 85:2149–2156. Automatic peptide synthesizers are commercially available from numerous suppliers, such as Applied Biosystems, Foster City, Calif.

A second method for synthesizing the proteins and polypeptides of the present invention involves the expression in cultured mammalian cells of recombinant DNA molecules encoding the desired $GAD_{65}$ gene or a portion thereof. Mammalian expression systems, such as Chinese hamster ovary (CHO) cells, effect post-translational modification of the proteins and polypeptides thereby enhancing the immunological similarity of the synthetic products with the native forms of $GAD_{65}$. Furthermore, baculovirus and yeast expression systems often effect the necessary post-translational modifications. The $GAD_{65}$ gene may itself be natural or synthetic, with the natural gene obtainable from cDNA or genomic libraries using degenerate probes based on the known amino acid sequence set forth in Julien et al., supra. Alternatively, polynucleotides can be synthesized based on the reported DNA sequence by well known techniques. For example, single-stranded DNA fragments can be prepared by the phosphoramidite method described by Beaucage and Carruthers (1981), *Tett. Letters* 22:1859–1862. A double-stranded fragment can then be obtained by synthesizing the complementary strand and annealing the strands together under appropriate conditions or by adding the complementary strand using DNA polymerase with an appropriate primer sequence.

The natural or synthetic DNA fragments coding for the desired $GAD_{65}$ protein or fragment are then incorporated in DNA constructs. Usually, the DNA constructs are capable of replicating in prokaryotic hosts in order to facilitate initial manipulation and multiplication of the construct. After a sufficient quantity of the construct has been obtained, it is introduced into the genome of cultured mammalian, insect (e.g., SF9), yeast or other eukaryotic cell lines.

DNA constructs suitable for introduction to bacteria or yeast usually include a replication system recognized by the host, the $GAD_{65}$ DNA fragment encoding the desired protein or polypeptide product, transcriptional and translational initiation and regulatory sequences joined to the 5'-end of the structural DNA sequence, and transcriptional and translational termination regulatory sequences joined to the 3'-end of the structural sequence. The transcriptional regulatory sequences includes a heterologous promoter which is recognized by the host.

Conveniently, available cloning vectors which include the replication system and transcriptional and translational regulatory sequences together with an insertion site for the $GAD_{65}$ DNA sequence can be employed. For transformation of mammalian and other eukaryotic cell lines, co-transfection of the cell lines in the presence of suitable marker, such as the DHFR gene, can be employed. Transfection can also be accomplished using chemical or electroporation techniques.

$GAD_{65}$ polypeptides are purified, if desired, from cell cultures expressing recombinant genes by a variety of methods. For example, the polypeptide can be purified by a combination of conventional methods based on differences in size (gel filtration), charge (ion exchange chromatography), hydrophobicity (phenyl-sepharose chromatography) or other physical parameters. Immunoadsorbent affinity chromatography bearing antibodies specific for $GAD_{65}$ can also be used. Affinity chromatography is performed by first linking the antibodies to a solid phase support and then contacting the linked antibodies with a source of the polypeptides to be purified, e.g., lysates of CNS or pancreatic cells or cells which have been recombinantly modified to produce $GAD_{65}$, or of supernatants of cells which have been recombinantly modified to secrete $GAD_{65}$ when cultured.

A third method for synthesizing GAD65 polypeptides is to employ an in vitro transcription/translation system. DNA encoding a GAD65 polypeptide is cloned on an expression vector as described supra. The expression vector is then transcribed and translated in vitro in, e.g., a rabbit reticulocyte lysate system. The translation product can be used directly or first purified. Polypeptides resulting from in vitro translation typically do not contain the post-translation modifications present on polypeptides synthesized in vivo. For example, in vitro translated $GAD_{65}$ polypeptides are typically not palmitoylated at amino acids 31 and 45, and these amino acids would not necessarily have to be mutated or deleted to confer solubility in aqueous solvents.

For use in purification, antibodies to $GAD_{65}$ can be obtained by injecting $GAD_{65}$ fragments thereof into a wide variety of vertebrates in accordance with conventional techniques. Suitable vertebrates include mice, rats, sheep, and goats. Usually, the animals are bled periodically with successively bleeds having improved titer and specificity. The antigens may be injected intramuscularly, interperitoneally, subcutaneously, or the like, usually, in a complete or incomplete Freund's adjuvant. Monoclonal antibodies can be prepared by well-known techniques. Monoclonal Fab fragments can also be produced. See, e.g., Huse et al. (1989), *Science* 246:1275–1281.

The $GAD_{65}$ fragments of the present invention can be used either as a component of a crude lysate or in substantially pure form. "Substantially pure" means that a polypeptide is typically at least about 50% w/w (weight/weight) purity, as well as being substantially free from interfering proteins and contaminants. Sometimes the fragments are isolated or synthesized in a purity of at least about 80% w/w and, more preferably in at least about 95% w/w purity. However, using conventional protein purification techniques, homogeneous peptides of at least 99% w/w can be obtained.

C. Epitope Mapping

The polypeptide fragments of the present invention contain at least one epitope reactive with at least one class of autoantibody against the $GAD_{65}$ protein. The localization of epitopes within the $GAD_{65}$ protein is facilitated by thb availability of monoclonal antibodies reactive with $GAD_{65}$ that have been derived from a patient suffering from, or at risk of, IDDM or stiff man syndrome. Procedures for isolating and screening human monoclonal antibodies are described by Richter et al. (1992), *Proc. Natl. Acad. Sci. (USA)*, 89:8467–71 (hereby incorporated by reference in its entirety for all purposes). Briefly, a number of EBV-immortalized β-cell lines were derived from the peripheral blood of newly diagnosed IDDM patients. IgG-producing monoclonal B-cell lines were screened for binding to the 64 kDa pancreatic β-cell autoantigen by indirect immunofluorescence staining of frozen sections of human pancreas. The cell lines were stabilized by repeated single-cell cloning. Six stable cell lines isolated by this method produced monoclonal antibodies designated MICAs 1–6.

Human monoclonal antibodies against $GAD_{65}$, or polyclonal sera from patients having, or at risk of, IDDM or stiff man syndrome, are used to map $GAD_{65}$ epitopes useful for detecting the presence of $GAD_{65}$ autoantibodies. $GAD_{65}$ epitopes are mapped by testing a collection of $GAD_{65}$ peptides (prepared as in Section I.B) for binding to monoclonal antibodies or polyclonal sera. Binding is usually detected by a conventional immunoprecipitation assay. Binding can also be detected by Western blotting. However, because Western blotting is performed under denaturing conditions, it detects binding to only linear epitopes. Comparison of results from immunoprecipitation and Western blotting indicates which epitopes are linear and which are conformational.

In another approach, epitopes can be mapped by protein footprinting. In this technique, a $GAD_{65}$ protein or peptide is allowed to bind to an antibody and then exposed to a protease. The residues of $GAD_{65}$ binding to the monoclonal antibody are protected from proteolytic degradation, and identified by amino acid sequencing.

D. $GAD_{65}$ Fragments as Diagnostic Reagents

Identification of the sequence co-ordinates of $GAD_{65}$ epitopes reactive with autoantibodies allows production of $GAD_{65}$ fragments containing one or more such epitopes as diagnostic reagents. The sequence co-ordinates used to define $GAD_{65}$ fragments refer to amino acids from the 585-amino-acid rat $GAD_{65}$ sequence disclosed by Bu et al. (1992), *Proc. Natl. Acad. Sci. (USA)* 89: 2115–2119 and shown in FIG. 1, corresponding amino acids from the 585-amino acid human $GAD_{65}$ sequence disclosed by Bu et al. (also shown in FIG. 1), or corresponding amino acids from any other cognate or analog $GAD_{65}$ polypeptides, when such polypeptides are maximally aligned with the rat $GAD_{65}$ sequence of Bu et al. A protein is considered "maximally aligned" with the rat $GAD_{65}$ sequences according to the criteria of any one of the following references: Smith & Waterman (1981), *Adv. Appl. Math.* 2: 482; Needleman & Wunsch (1970), *J. Mol. Biol.* 48: 443; Pearson & Lipman (1988), *Proc. Natl. Acad. Sci. (U.S.A.)* 85: GAP, BESTFIT, FASTA, and TFASTA in the Wisconsin Genetics Software Package, Genetics Computer Group, 575 Science Dr., Madison, Wis. (each of which is incorporated by reference in its entirety for all purposes). Usually, analog proteins are encoded by nucleic acids that have the capacity to hybridize to DNA encoding the rat $GAD_{65}$ protein under stringent conditions.

Usually, $GAD_{65}$ fragments are free of N-terminal amino acids that limit solubility in aqueous solvents. Such amino acids can be removed by deletion and/or substitution. The N-terminal amino acids that are removed or mutated can comprise over two hundred amino acids from the N-terminal of the $GAD_{65}$ protein. However, some $GAD_{65}$ fragments of the invention are free of shorter N-terminal segments, comprising for example, about 8, 25, 50, 75, 100, and 150 amino acids from the N-terminal region. At minimum, amino acids from about positions 24–31 should be removed or substituted. Preferably, amino acid 45 should also be removed or substituted. Thus, for example, a fragment having a deletion of amino acids 1–31, and, preferably, a substitution of an alanine residue for a cysteine residue at amino acid 45 is soluble. A fragment having a deletion of amino acids 1–45 is also soluble.

Alternatively, soluble $GAD_{65}$ polypeptides can be produced by synthesising the polypeptides under conditions such that post-translational modifications do not occur. For example, polypeptides can be synthesized in an in vitro translation system or on a peptide synthesizer. See Section IB, supra. Polypeptides can also be synthesized in vivo in the presence of an inhibitor of lipid attachment such as cerulenin.

Often the amino acids that are removed to confer solubility of a $GAD_{65}$ peptide are contiguous, but this is not essential. All that is required is that sufficient N-terminal amino acid sequence be deleted for the remaining protein fragment to be soluble or substantially soluble in an aqueous medium, such as media typically employed in protein purification or for immunoassay.

Surprisingly, the results presented in Example 5 indicate that deletion of at least the first 244 amino acids from the N-terminal of $GAD_{65}$ does not impair reactivity of the principal $GAD_{65}$ epitopes against IDDM autoantibodies. Thus, a soluble fragment lacking the 244 N-terminal amino acids, but containing the remaining $GAD_{65}$ amino acids (i.e., a contiguous sequence from amino acids 245 to 585 (the C-terminal amino acid) is reactive with all three classes of IDDM autoantibodies defined by MICA1/MICA3, MICA4/MICA6 and MICA2. See Example 5. Also suitable are naturally occurring soluble fragments of $GAD_{65}$ or $GAD_{67}$ that result from proteolytic degradation or alternative splicing patterns. These fragments have been detected in extracts of brain, β-cells and recombinant expression systems. The fragments usually have a molecular weight of about 55–57 kDa and lack about 65–80 amino acids from the N-terminal. See, e.g., Christgau et al. (1992), *J. Cell Biol.* 118:309–320. The absence of these N-terminal amino acids renders the fragments substantially soluble in aqueous solvents. Naturally occurring fragments are conveniently purified by immunoaffinity chromatography using an antibody specific for an epitopes contained within about amino acids 60–120. The same antibody can be used to immobilize the fragments for immunoassay.

The invention also provides soluble fragments having modifications both at the N-terminal (to render the fragment soluble) and elsewhere. One such fragment is substantially free of at least about forty-one amino acids from the C-terminal (i.e., amino acids 545–585). A fragment substantially free of the forty-one C-terminal amino acids is able to recognize IDDM autoantibodies having the specificity of MICA4/MICA6, but not with the specificity of MICA1/MICA3 or MICA2.

Another fragment provided by the invention is rendered soluble by deletion or substitution of N-terminal amino acids and is also substantially free of a segment from about amino acid 245 to 295. This fragment is able to recognize IDDM autoantibodies with the specificity of MICA2, but not autoantibodies having the specificity of MICA1/MICA3 or MICA2/MICA4.

Some fragments are substantially free of amino acids 70–101 and/or 1–20, and are thereby rendered free of two nonconformational epitopes reactive with autoantibodies diagnostic of stiff man syndrome. However, such fragments are reactive with stiff man syndrome autoantibodies that recognize conformational epitopes. Fragments that react with one or more autoantibodies diagnostic of IDDM but do not react with any class of autoantibodies diagnostic of SMS may be produced by further localizing IDDM epitopes to peptide fragments of minimal, or near minimal, length. These fragments may constitute sequences of $GAD_{65}$ amino acids, or analog miniproteins, as described by Ladner et al., U.S. Pat. No. 5,223,409 (1993) (incorporated by reference in its entirety for all purposes). Fragments or miniproteins could then be screened for absence of reactivity with sera from SMS patients.

The invention also provides fragments containing at least one linear (or nonconformational) epitope reactive with SMS autoantibodies. As noted above, these epitopes are contained within amino acids 1–20 (amino acids 1–10 are particularly important for binding) and 70–101. For a functional epitope, usually at least about 6, 8 or 10 contiguous amino acids and more usually, all, or substantially all (i.e., 70, 80, 90 or 95%) of the specified segments are present. The SMS epitopes are both linear and therefore reactive with SMS autoantibodies irrespective of the conformation of the rest of the molecule. Thus, even a fragment consisting essentially of amino acids from about 70–101 or amino acids from about 1–20 and lacking flanking amino acids is reactive with SMS autoantibodies. Of course, such a fragment lacks epitopes required for binding to the principal classes of IDDM autoantibodies. However, longer fragments are provided in which one or more other epitopes diagnostic of IDDM are present. Thus, for example, a fragment comprising amino acids 1–20, 70–101 and 245–585 would contain epitopes for all three principal classes of IDDM autoantibodies, as well as for conformational and nonconformational classes of SMS autoantibody.

The provision of $GAD_{65}$ fragments having autoantibody-binding epitopes offers numerous advantages compared with intact $GAD_{65}$. The fragments of the invention usually have a high solubility in aqueous solvents in contrast to intact $GAD_{65}$, which requires detergent for solubilization and has a tendency to form aggregates and precipitate even in the presence of detergent. Formation of aggregates can mask epitopes and thereby reduce sensitivity and accuracy of autoantibody detection. Furthermore, the presence of detergent is often detrimental for binding to ELISA plates. Although $GAD_{65}$ can be solubilized using ionic detergents and denaturing solvents, such conditions are incompatible with maintaining conformational epitopes. Authentic conformation is particularly important for detecting autoantibodies to IDDM of the MICA1/MICA3 or MICA4/MICA6 specificity. See Example 4.

A further advantage of the present fragments is that they allow distinction between IDDM and stiff man syndrome. For example, a fragment consisting essentially of amino acids 1–20 and/or 70–101 is reactive only with SMS autoantibodies, a fragment of amino acids 245–585 is reactive with IDDM autoantibodies and SMS conformational autoantibodies, and a fragment comprising amino acids 1–20 and/or 70–101 and 245–585 is reactive with all of these classes of autoantibodies.

A still further advantage of the present fragments is their capacity to distinguish different temporal stages in the progression of IDDM. As discussed in Example 7, it is likely that autoantibodies having the binding specificity of MICA1/MICA3 appear first, followed by autoantibodies having the specificity of MICA4/MICA6, followed by autoantibodies having the specificity of MICA2. Thus, the relative proportions of these different autoantibodies in a patient's serum allows monitoring of the disease through its primary phases to clinical onset and beyond. The different autoantibodies are easily distinguished using different fragments as diagnostic reagents. A fragment containing a GAD segment from about amino acid 245–585 binds all three classes of autoantibodies, a fragment from about amino acid 245–545 binds only the MICA4/6 class and a fragment from about amino acid 445–585 binds only the MICA2 class.

E. Other Diagnostic Reagents

The $GAD_{65}$ fragments of the invention can be used to immunize laboratory animals and thereby derive monoclonal antibodies against the fragments. The monoclonal antibodies are then in turn used to immunize further animals and generate anti-idiotypic antibodies. An anti-idiotype whose binding to the primary antibody is inhibited by a $GAD_{65}$ fragment is selected. Because both the anti-idiotypic antibody and $GAD_{65}$ fragment bind the primary immunoglobulin, the anti-idiotypic immunoglobulin may represent the "internal image" of an epitope and thus may substitute for the $GAD_{65}$ fragment. The anti-idiotypic antibodies are used in methods of diagnosis in essentially the same manner as the $GAD_{65}$ fragments.

II. Methods of Use

A. Diagnostic and Predictive Assays

The diagnostic methods of the present invention require techniques for detecting specific interaction between ligands (e.g., a $GAD_{65}$ fragment) and autoantibodies. The particular assay protocol chosen is not critical, and it is necessary only that the assay be sufficiently sensitive to detect a threshold level of the autoantigen which is considered to be positive. Suitable assays include both solid phase (heterogeneous) and non-solid phase (homogeneous) protocols. The assays can be run using competitive or non-competitive formats, and using a wide variety of labels, such as radioisotopes, enzymes, fluorescers, chemiluminescers, spin labels, and the like.

$GAD_{65}$ autoantibodies are often detected by an immunoprecipitation technique, in which $GAD_{65}$ polypeptides are labelled with an isotope or ligand. Polypeptides may be labelled during synthesis (e.a., by adding $^{35}$S-methionine to an in vitro translation system or cellular expression system), or after synthesis. The labelled polypeptide is incubated with a sample of serum to form immunocomplexes. The immunocomplexes are precipitated with polyethylene glycol, or staphylococcus aureus or protein A immobilized on beads. After several washings, the immunoprecipitates are counted to assess how much radioactive antigen has been precipitated. Optionally, an unlabelled $GAD_{65}$ polypeptide may also be added to compete with the labelled polypeptide for binding to autoantibodies.

Some assays rely on heterogeneous protocols where the ligand is bound to a solid phase that is used to separate the ligand-autoantibody complex that forms when autoantibody is present in a serum sample. The ligand may be conveniently immobilized on a variety of solid phases, such as dipsticks, particulates, microspheres, magnetic particles, test tubes, microtiter wells, and nitrocellulose or nylon membranes and the like.

The solid phase is exposed to a serum sample so that the autoantibody, if any, is captured by the ligand. By then removing the solid phase from the serum sample, the captured autoantibody is removed from unbound autoantibodies and other contaminants in the serum sample. The captured autoantibody can then be detected using the non-competitive "sandwich" technique where labelled ligand for the autoantibody is exposed to the washed solid phase. Alternatively, competitive formats rely on the prior introduction of a labelled $GAD_{65}$ antibody to the serum sample so that labelled and unlabelled forms compete for binding to the solid phase. Such assay techniques are well known and well described in both the patent and scientific literature. See, e.g., U.S. Pat. Nos. 3,791,932; 3,817,837; 3,839,153; 3,850,752; 3,850,578; 3,853,987; 3,867,517; 3,879,262; 3,901,654; 3,935,074; 3,984,533; 3,996,345; 4,034,074; and 4,098,876 (each of which is incorporated by reference in its entirety for all purposes). Enzyme-linked immunosorbent assay (ELISA) methods are described in detail in U.S. Pat. Nos. 3,791,932; 3,839,153; 3,850,752; 3,879,262; and 4,034,074 (each of which is incorporated by reference in its entirety for all purposes). ELISA assays detect very low titers of autoantibodies.

Autoantibodies can also be detected by solid-phase radioimmunoassay (RIA). The solid phase is exposed to the serum sample in the presence of radiolabelled antibodies that compete for binding to the immobilized ligand. In this assay, the amount of radiolabel bound to the solid phase is inversely related to the amount of autoantibodies initially present in the serum sample. After separation of the solid phase, non-specifically bound radiolabel is removed by washing, and the amount of radiolabel bound to the solid phase determined. The amount of bound radiolabel is, in turn, be related to the amount of autoantibodies initially present in the sample.

In a further variation, when the ligand is a $GAD_{65}$ fragment containing sufficient amino acid sequence to retain L-glutamate 1-carboxylase activity, autoantibody is detected by quenching of enzymic activity on binding of autoantibody.

At least three improved methods of detecting $GAD_{65}$ autoantibodies stem in part from the discovery that substantial amounts of $GAD_{65}$ N-terminal sequence are not required for binding to $GAD_{65}$ autoantibodies. In some methods, $GAD_{65}$ autoantibodies are detected using soluble fragments of $GAD_{65}$. Fragments are rendered soluble by deletion or substitution of N-terminal amino acids. As discussed supra, at least about amino acids 24–31 and, preferably, amino acid 45 must be removed and/or substituted. All of the soluble fragments discussed supra can be used. The advantages of methods of diagnoses using soluble fragments, namely, ease of purification of the fragment, and capacity to perform the assay under nondenaturing conditions, have been discussed supra (see Section I.D.).

The discovery of the autoreactive epitopes in the middle and C-terminal part of the $GAD_{65}$ molecule not only allows deletion of some or all of amino acids 1–244 to create soluble fragments, but frees much of the N-terminal region for other useful modifications. For example, radioactive and/or immobilizing moieties can be attached to the N-terminal part of the enzyme without affecting the principal autoantibody-binding epitopes. Thus, some methods of the invention utilize a fusion protein as the diagnostic reagent, and the fusion protein may, or may not, be soluble. The fusion protein has two peptide components. One component is a $GAD_{65}$ protein, or a peptide thereof, having at least one epitope reactive with a $GAD_{65}$ autoantibody. The second peptide is usually unrelated to $GAD_{65}$ and is engineered to have one or more suitable properties for purification of the fusion protein and/or use of the fusion protein as a diagnostic reagent. For instance, an amino terminal extension with recognition sites for a monoclonal antibody and for a site specific protein kinase is described by Blanar & Rutter (1992), *Science* 256:1014–1018 (incorporated by reference in its entirety for all purposes). Fusion of such an N-terminal extension product to a $GAD_{65}$ protein or fragment allows the fusion protein to be purified in a single step by immunoaffinity chromatography using the monoclonal antibody to the N-terminal extension. The fragment is eluded by competing amounts of the corresponding peptide, rather than extremes in pH which damage the conformational diabetic epitopes. The molecule can then be immobilized to ELISA plates via the monoclonal antibody recognizing the N-terminal extension peptide. When immobilized in this orientation, the epitopes binding the principal autoantibodies diagnostic of IDDM are distal from the plate and therefore available for binding. This eliminates the problem of steric hinderance that can result from coating the plates directly with the antigen. Furthermore, the kinase site allows for the labeling of the molecule with $^{32}$p for very sensitive and rapid radioimmunoassays after its purification by immunoaffinity chromatography using the monoclonal antibody. For example, a heart muscle kinase site can be labelled with $^{32}$P-ATP and heart muscle kinase.

In other methods of the invention, a $GAD_{65}$ protein or peptide fragment thereof is immobilized to a solid support using a monoclonal antibody specifically reactive with an epitope occurring within N-terminal amino acids 1–244. These amino acids are not required for binding of the principal IDDM autoantibodies to $GAD_{65}$, and thus attachment via the N-terminal sequence does not impair binding to these autoantibodies. A suitable antibody for anchoring the N-terminal sequence is raised by injecting a peptide formed from amino acids 1–244 (or a subfragment thereof) into a laboratory animal, such as rabbits or mice, and isolating a monoclonal antibody by conventional methods. This approach does not necessitate the addition of the amino terminal extension to the $GAD_{65}$ molecule described above.

Immobilization of the $GAD_{65}$ fragment via the antibody has at least two advantages. First, $GAD_{65}$ fragments can be purified by immunoaffinity chromatography (a mild procedure which preserves the conformation of autoimmune epitopes). Purified $GAD_{65}$ fragments are then available for use in, e.g., immunoprecipitation assay. Alternatively, a crude preparation of $GAD_{65}$ is immobilized via the antibody to ELISA plates. $GAD_{65}$ binds to the plates in an orientation which allows the epitopes to be accessible to IDDM autoantibodies. Impurities are washed away, while the $GAD_{65}$ remains bound. Autoantibodies are then detected by ELISA.

All of the three types of improved methods of diagnosis described can be used to detect one or more of the three principal classes of autoantibodies diagnostic or IDDM as described in Examples 5 and 7. Detection of these autoantibodies indicates that a patient has, or is at risk of IDDM (i.e., the patient is prediabetic). Pre-diabetic patients have circulating autoantibodies to $GAD_{65}$ but have not yet suffered sufficient damage to the insulin-producing β-cell to be clinically identified as having IDDM. The assays are also useful for monitoring the effect of immunotherapy to block or prevent autoimmune reactions to the β-cell and for monitoring the progress of the disease from pre-diabetes to clinical diabetes. The assays are also useful for monitoring the status of transplanted pancreatic β-cells in diabetic patients, who have undergone an islet cell graft, where the presence of $GAD_{65}$ autoantibodies indicates an adverse immune response to the transplanted cells.

Methods of diagnosis using N-terminal fusion proteins are equally applicable to detecting autoantibodies diagnostic of stiff man syndrome that bind to a linear epitope formed between amino acids 1–20 or 70–101. Because these epitopes are nonconformational, the addition of an N-terminal peptide is unlikely to affect their binding capacity to SMS autoantibodies. However, the other improved methods involving deletion of substantial amounts of N-terminal sequence or anchorage of a $GAD_{65}$. protein or fragment via its N-terminal sequence must be modified for detection of stiff man syndrome. For example, while substantial lengths of N-terminal sequence can be deleted to produce a soluble peptide, the deleted sequence should not usually encompass amino acids 1–20 or 70–101. Similarly, in methods in which the $GAD_{65}$ peptide is anchored to a support via a monoclonal antibody, the monoclonal antibody must bind to an epitope that does not overlap the 1–20 and 70–101 epitopes, and is usually at least 10, more usually at least 50 amino acids distil to these epitopes.

The invention also provides improved methods for detecting certain $GAD_{65}$ autoantibodies using insoluble $GAD_{65}$ fragments. The Examples disclose that one class of IDDM autoantibodies (exemplified by MICA2) and two classes of SMS autoantibodies recognize nonconformational epitopes. Accordingly, fragments containing these epitopes can be purified by solubilization in ionic detergents without concern that loss of conformation will impair binding capacity to autoantibodies binding the nonconformational epitopes. Thus, in these methods, intact $GAD_{65}$ or insoluble fragments thereof, comprising a nonconformational epitope (i.e., including at least one segment from amino acid 1–20, 70–101 or 545–585), are purified in denaturing conditions, and then used to detect $GAD_{65}$ autoantibodies, without renaturation.

3. Methods of Differential Diagnosis

In another aspect of the invention, methods of diagnosis are provided that distinguish between IDDM and stiff man syndrome, and/or between different temporal stages in progression of IDDM. Some methods detect autoantibodies diagnostic of stiff man syndrome without detecting autoantibodies diagnostic of IDDM. In these methods, the diagnostic reagent is a $GAD_{65}$ fragment having an epitope reactive with a stiff man syndrome autoantibody and free of an epitope reactive with an IDDM autoantibody. For example, a fragment comprising amino acids 1–20 and/or amino acids 70–101 and substantially free of amino acids 245–585, so as to lack all of the three principal IDDM autoantibody-binding epitopes, is suitable. A fragment consisting essentially of amino acids 1–101 is also suitable.

Other methods are provided for monitoring the temporal progression of IDDM. These methods distinguish between early and late epitope recognition and thereby estimate the duration of the immune response. The methods stem, in part, from the identification of three epitopes that bind distinct classes of autoantibodies diagnostic of different temporal stages of progression of the disease. In these methods, a serum sample from a patient is exposed to a first $GAD_{65}$ fragment having an epitope reactive with a first $GAD_{65}$ autoantibody. The presence or absence of a specific interaction with a $GAD_{65}$ autoantibody, which may or may not be present in the serum, is detected. These steps are then repeated, using a second $GAD_{65}$ fragment having an epitope reactive with a second $GAD_{65}$ autoantibody.

Suitable $GAD_{65}$ fragments for differential temporal diagnosis of IDDM have been discussed in section I.D., supra. Briefly, a fragment comprising a contiguous sequence of amino acids 245–585 contains epitopes reactive with all three principal classes of IDDM autoantibodies. These classes are autoantibodies having the binding specificity of MICA1/MICA3 (produced earliest), autoantibodies having the same binding specificity as MICA4/6 (produced second), and autoantibodies having the same binding specificity as MICA2 (produced third). A fragment lacking approximately the C-terminal 41 amino acids (i.e., 545–585) is reactive only with autoantibodies of the MICA4/MICA6 class. A fragment comprising amino acids 545–585 and substantially free of amino acids 245–295 is reactive only with autoantibodies of the MICA2 class. Thus, for example, specific interaction with a 245–585 amino acid fragment, but not the other two classes of fragments indicates a patient in the early phases of autoimmune response to the β-cell epitope. Specific interaction with both a 245–585 fragment and a fragment lacking the 41 terminal amino acids indicates a patient at an intermediate phase of autoimmune response. Reactivity with all three fragments indicates a later phase of immune response.

4. Predictive Value of $GAD_{65}$ Autoantibodies for Diagnosis of IDDM

After onset of clinical symptoms of IDDM, about seventy percent of patients produce at least one class of $GAD_{65}$ autoantibodies. By contrast, only about 1–2% of normal patients produce these autoantibodies. See, e.g., Karlsen et al., *Diabetes* 41, 1355–1359 (1992); Hagopian et al, *Diabetes* 42, 631–636 (1993) (each of which is incorporated by reference in its entirety for all purposes). Thus, detection of $GAD_{65}$ autoantibodies is strongly diagnostic of established IDDM.

Detection of $GAD_{65}$ autoantibodies in normal individuals is also highly predictive in identifying individuals at risk of developing IDDM. In one study, serum samples from initially-healthy children were analyzed over an eleven-year time span. Seven of the samples taken at the beginning of the study were found to contain at least one class of $GAD_{65}$ autoantibodies. Five of the seven children from whom these samples were derived proceeded to develop IDDM over the course of the study. By contrast, of one hundred children whose initial samples were free of GADS5 autoantibodies, only one developed IDDM.

B. Methods of Treatment

1. Immunotolerance

The soluble $GAD_{65}$ fragments described above are administered to a patient in vivo to induce immunogenic tolerance to antigenic determinants on the soluble fragment. Of course, care must be taken that administration of $GAD_{65}$ fragments does not perpetuate the immune response. The nature of response (i.e., immunogenic or tolerogenic) depends on the dose, physical form and route of administration of antigen. High or low doses of an antigen often lead to immunotolerance, whereas intermediate doses may be immunogenic. Monomeric forms of antigen are usually tolerogenic, whereas high molecular weight aggregates are likely to be immunogenic. Oral, nasa, gastric or intravenous injection of antigen frequently leads to tolerance, whereas intradermal or intramuscular challenge especially in the presence of adjuvants favors an immunogenic response. Oral administration of an autoimmune antigen has been shown to protect against development of experimental allergic encephalomyelitis in animal models, and to suppress rheumatoid arthritis in animal models and in clinical trials. See Marx, *Science* 252, 27–28 (1991); Trentham et al., *Science* 261, 1727–1730 (1993) (each of which is incorporated by reference in its entirety for all purposes). Nasal administration of an autoantigen has also been reported to confer protection against experimental allergic encephalomyelitis, and is a preferred route for administration of small fragments. See Metzler & Wraith, *International Immunology* 5, 1159–1165 (1993) (incorporated by reference in its entirety for all purposes). In some methods, immunotolerance is induced under cover of immunosuppressive treatment. See Cobbold et al., WO90/15152 (1990) (which is incorporated by reference in its entirety for all purposes).

Tolerance is imparted by elimination of, or induction of nonresponsiveness in, autoimmune T or B cells. It can be induced in part by activation of suppressor mechanisms by the soluble fragment, which suppress cellular and humoral responses directed toward the fragment. Suppression of cellular responses is of particular importance in preventing destruction of pancreatic β-cells in IDDM. Thus, $GAD_{65}$ fragments that specifically bind to a $GAD_{65}$ autoreactive T-cell ($GAD_{65}$ T-cell) are particularly suitable for inducing immunotolerance. See, e.g., Kaufman et al., (1993), *Nature* 366:69–71; Tisch et al. (1993), *Nature* 366, 71–75 (which are hereby incorporated by reference in their entirety for all purposes). Suppression of humoral responses is believed to be of particular importance in preventing impairment of neurons in stiff man syndrome.

In some embodiments, the generation of nonresponsiveness and consequent impairment of autoimmune response is facilitated by coupling the soluble $GAD_{65}$ fragments of the present invention to immunoglobulins, e.g., IgG, or to lymphoid cells from the patient being treated. See Bradley-Mullen (1982), *Annals N.Y. Acad. Sci.* 392: 156–166 (incorporated by reference in its entirety for all purposes).

2. Inhibition of T-cell Activation by $GAD_{65}$ Blocking Peptides

Soluble $GAD_{65}$ fragments are also used to inhibit activation of T-cells by blocking binding of autoantigens to an MHC receptor using, e.g., the method described by Wraith et al. (1989), *Cell* 59: 247–255 (incorporated by reference in its entirety for all purposes). $GAD_{65}$ fragments for use in these methods are first subjected to a modification of their naturally occurring sequence. The modification can be effected, e.g., by in vitro mutagenesis of $GAD_{65}$ DNA fragments, or by de novo synthesis of analog peptides on a peptide synthesizer. The modifications introduced into the soluble $GAD_{65}$ fragments serve to reduce or eliminate the binding affinity of the soluble $GAD_{65}$ fragments for a T-cell receptor, while maintaining, or preferably enhancing, the fragments' capacity to bind to MHC molecules. Molecules with the desired binding specificity can be screened by e.g., phage-display technology. See, e.g., Devlin, WO91/18980 (incorporated by reference in its entirety for all purposes). Soluble $GAD_{65}$ fragments modified in this manner compete with $GAD_{65}$ autoantigens for binding to MHC molecules, but are unable to activate T-cells when so bound. Thus, the amount of authentic $GAD_{65}$ autoantigen bound to MHC receptors, and the extent of the T-cell-mediated immune response effected by such binding are reduced.

3. Elimination of T-cells Specific for $GAD_{65}$ Autoantigens

Another approach for treating autoimmune diseases is based on induction of a B-cell immune response directed against T-cells responsible for mediating an autoimmune disease. See, generally, Sinha et al. (1990), *Science* 248: 1380–1388. In these methods, soluble $GAD_{65}$ fragments are used for propagation and isolation of clonal isolates of helper or cytotoxic T-cells specific for the $GAD_{65}$ autoantigen. These T-cells or components thereof are then used as a vaccine to induce a B-cell immune response.

Peripheral blood lymphocytes are collected from an individual suffering from, or at risk of, IDDM or stiff man syndrome. Helper or cytotoxic T-cells within the peripheral blood lymphocytes are stimulated by exposure to a soluble $GAD_{65}$ peptide, using methods well known in the art (see, e.g., *Leukocyte Typing II, Vol.* 1 (Reinherz et al. eds., Springer Verlag, N.Y., 1986) (incorporated by reference in its entirety for all purposes). Usually, other mitogens and growth enhancers are present, e.g., phytohemagglutinin, interleukin 2, and the like. Clones of T-helper cells or cytotoxic T-cells are isolated from these cultures. The clones of T-cells can then be attenuated (e.g., by exposure to radiation) before incorporation into a pharmaceutical composition for in vivo administration. As an alternative to attenuation, portions of the T-cell, which are capable of acting as immunogens, but which themselves lack the T-helper or T-cytotoxic activity of an intact cell are isolated, e.g., by biochemical fractionation. The T-cell receptor or immunogenic fragments thereof, which are capable of an immune response specific for a clonal isolate of T-cells, are particularly suitable. Fragments of T-cell receptors are prepared by conventional recombinant DNA technology.

C. Pharmaceutical Compositions $GAD_{65}$ soluble fragments or T-cell components can be incorporated into pharmaceutical compositions useful to attenuate, inhibit, or prevent the destruction of pancreatic β-cells associated with the onset of insulin-dependent diabetes mellitus, or the impairment of neurons associated with stiff man syndrome. The compositions should contain a therapeutic or prophylactic amount of at least one soluble fragment of $GAD_{65}$ and/or a T-cell component (e.g., a T-cell receptor fragment) in a pharmaceutically-acceptable carrier. The pharmaceutical carrier can be any compatible, non-toxic substance suitable to deliver the polypeptides to the patient. Sterile water, alcohol, fats, waxes, and inert solids may be used as the carrier. Pharmaceutically-acceptable adjuvants, buffering agents, dispersing agents, and the like, may also be incorporated into the pharmaceutical compositions. The concentration of the $GAD_{65}$ peptide or other active agent in the pharmaceutical composition can vary widely, i.e., from less than about 0.1% by weight, usually being at least about 1% by weight to as much as 20% by weight or more.

For oral administration, the active ingredient can be administered in solid dosage forms, such as capsules, tablets, and powders, or in liquid dosage forms, such as elixirs, syrups, and suspensions. Active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that may be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

For nasal administration, the polypeptides can be formulated as aerosols. The term "aerosol" includes any gas-borne suspended phase of the compounds of the instant invention which is capable of being inhaled into the bronchioles or nasal passages. Specifically, aerosol includes a gas-borne suspension of droplets of the compounds of the instant invention, as may be produced in a metered dose inhaler or nebulizer, or in a mist sprayer. Aerosol also includes a dry powder composition of a compound of the instant invention suspended in air or other carrier gas, which may be delivered by insufflation from an inhaler device, for example. See Ganderton & Jones, *Drug Delivery to the Respiratory Tract*, Ellis Horwood (1987); Gonda (1990) *Critical Reviews in Therapeutic Drug Carrier Systems* 6:273–313; and Raeburn et al. (1992) *J. Pharmacol. Toxicol. Methods* 27:143–159.

A typical composition for intravenous infusion could be made up to contain 100 to 500 ml of sterile Ringer's solution and 100 to 500 mg of a $GAD_{65}$ peptide or a T-cell receptor peptide. A typical pharmaceutical compositions for intramuscular injection would be made up to contain, for example, 1 ml of sterile buffered water and 1 to 100 µg of the purified ligand of the present invention. Methods of preparing parenterally administrable compositions are well known in the art and described in more detail in various sources, including, for example, *Remington's Pharmaceutical Science* (15th ed., Mack Publishing, Easton, Pa., 1980) (incorporated by reference in its entirety for all purposes).

D. Methods of Administration

The pharmaceutical compositions of the present invention are usually administered intravenously or orally. Intradermal or intramuscular administration is also possible in some circumstances. The compositions can be administered for prophylactic treatment of individuals suffering from, or at risk of, IDDM or stiff man syndrome, as identified by the diagnostic methods of the present invention. For therapeutic applications, the pharmaceutical compositions are administered to a patient suffering from established diabetes in an amount sufficient to inhibit or prevent further β-cell destruction. For individuals at risk of IDDM or stiff man syndrome, the pharmaceutical composition are administered prophylactically in an amount sufficient to either prevent or inhibit immune destruction of the β-cells. An amount adequate to accomplish this is defined as a "therapeutically-effective dose." Such effective dosage will depend on the severity of the autoimmune response and on the general state of the patient's health, but will generally range from about 1 to 500 mg of purified ligand per kilogram of body weight, with dosages of from about 5 to 25 mg per kilogram being more commonly employed.

III. T-cells Specific for $GAD_{65}$ Fragments

Also provided are T-cells which have been stimulated by exposure to a soluble $GAD_{65}$ fragment. The T-cells are usually helper or cytotoxic T-cells. The T-cells are specific to $GAD_{65}$ fragments in that they exhibit specific binding to cells bearing such fragments complexed to MHC molecules. Also provided are components of the T-cells that are capable of inducing an immune response against $GAD_{65}$-specific T-cells. The components are usually T-cell receptors or fragments thereof. A receptor fragments must be capable of inducing an immune response against the clonal isolates of T-cells from which the fragment was derived.

The following examples are offered for illustration and not limitation.

EXAMPLES

Example 1
Expression of $GAD_{65}$ and $GAD_{67}$ Proteins

Recombinant baculovirus vectors expressing human and rat $GAD_{65}$ and human $GAD_{67}$ were constructed by ligating a 1.8 kb BamHI fragment of human $GAD_{65}$ cDNA clone into the BamHI site of the baculovirus vector pVL 941 (from Dr. D. Morgan, UCSF) and a 2.7 kb EcoRI fragment of human $GAD_{67}$ or a 2.4 kb EcoRI fragment of rat $GAD_{65}$ cDNA clone into the EcoRI site of the baculovirus vector pVL1392 (Invitrogen, San Diego, Calif.). Human $GAD_{65}$ and $GAD_{67}$ cDNAs were from Dr. A. Tobin, UCLA. Recombinant viruses were derived and isolated as described (see Christgau et al. (1992), *J. Cell Biol.* 118: 309–320) using established methods (Summers and Smith (1987), *Tex. Agric. Exp. Stn. Bull.* 1555:1–56). Recombinant baculovirus harboring full-length rat $GAD_{65}$ was described earlier (see Christgau et al. (1992), supra).

Example 2
Expression of Deletion Mutants of $GAD_{65}$

An N-terminal deletion mutant, lacking the first 101 amino acids, was generated by oligonucleotide-directed mutagenesis (see Kunkel (1985), *Proc. Natl. Acad. Sci. (USA)* 82:488–492) (incorporated by reference in its entirety for all purposes) of the full-length $GAD_{65}$ construct inserted into the pVL1392 vector, and expressed in insect cells.

Other deletion mutants were prepared for expression in COS-7 cells (American Type Culture Collection, Bethesda, Md.) as follows. Rat $GAD_{65}$ was subcloned into the KpnI and NotI sites of the pSV-SPORT vector (BRL, Gaithersburg, Md.). A collection of N-terminal and C-terminal deletion mutants of $GAD_{65}$ was generated by polymerase chain reaction (see Saiki et al. (1988), *Science* 239:487–494) (incorporated by reference in its entirety for all purposes) at predetermined sites using anchored primers. An internal deletion mutant lacking amino acids 363–422 was generated using the NsiI restriction sites in $GAD_{65}$. Similarly, BglII restriction sites were used to generate a hybrid molecule containing amino acids 1–95 from rat $GAD_{67}$ and amino acids 353–585 from rat $GAD_{65}$. Expression of protein fragments was analyzed by Western blotting using $GAD_{65}$-specific or $GAD_{67}$-specific antibodies as probes. These antibodies were obtained from the following sources: Mouse monoclonal GAD1 (see Gottlieb et al. (1986), *Neurobiol*. 83:8808–8812), which recognizes native forms of $GAD_{65}$ and $GAD_{67}$, was obtained from American Type Tissue Collection. Mouse monoclonal GAD6 (see Chang and Gottlieb (1988), *J. Neurosci*. 7:2123–2130), which is specific for $GAD_{65}$, was donated by Dr. D. Gottlieb (Washington University, St. Louis). A polyclonal rabbit antibody, 1266, raised against a C-terminal peptide of rat $GAD_{67}$, which recognizes both $GAD_{65}$ and $GAD_{67}$, was a gift from Dr. J. S. Petersen, Hagedorn Research Laboratory, Copenhagen. The K2 antiserum, which predominantly recognizes $GAD_{67}$, was a gift from Dr. A. Tobin, UCLA. Serum from a SMS patient was obtained from Dr. Vanda Lennon (Mayo Clinic, Rochester, N.Y.).

Protein fragments were purified from cell for assay as described by Christgau et al. (1991), *J. Biol. Chem*. 266: 21257–21264; Christgau et al. (1992), *J. Cell Biol*. 118:309–320).

Example 3
Monoclonal Antibodies Against $GAD_{65}$ Derived from an IDDM Patient

The ability of a set of monoclonal antibodies derived from a type 1 diabetic patient (MICAs 1–6, see Richter et al., supra) to recognize native human $GAD_{65}$ and/or $GAD_{67}$ proteins expressed in Sf9 insect cells or in COS-7 cells was examined. Binding of antibodies to $GAD_{65}$ was assayed by immunoprecipitation as described by Christgau et al. (1992), supra; Baekkeskov et al. (1990), Nature 347:151–157).

Figure 2:
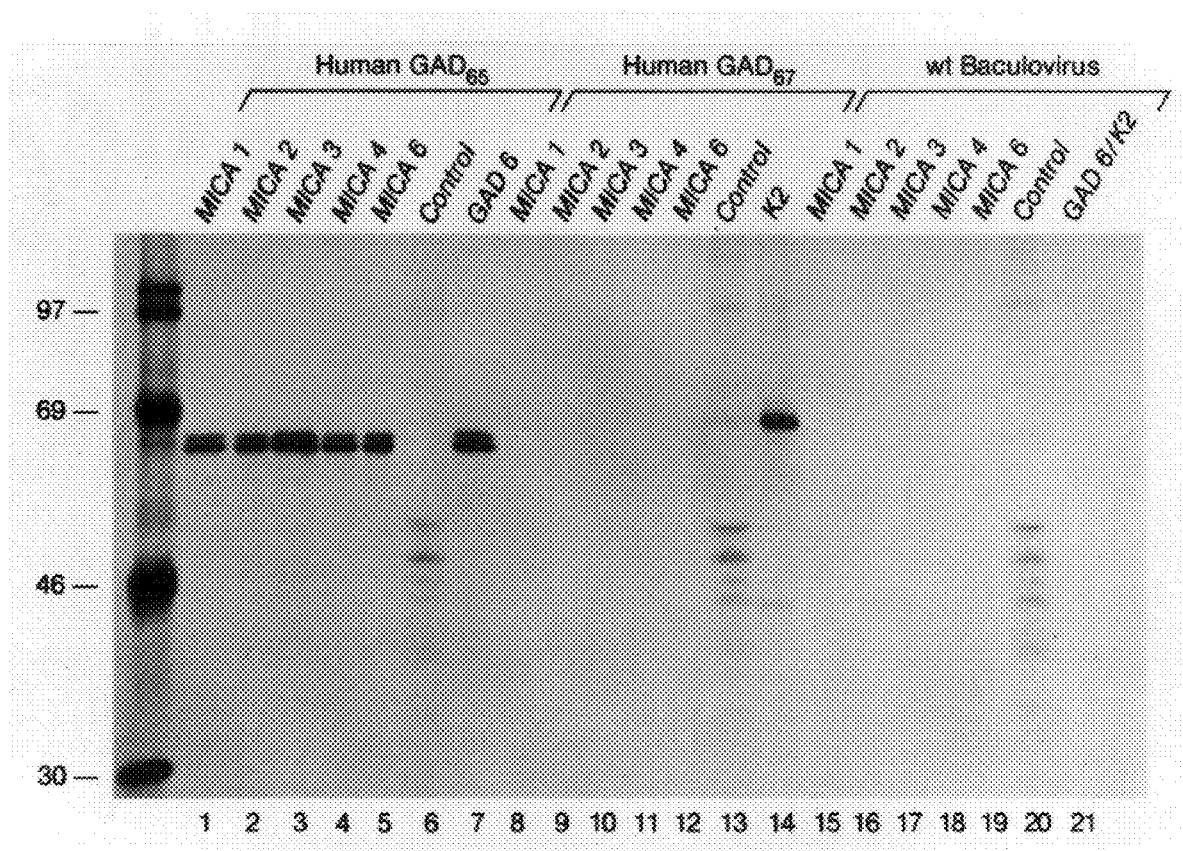
FIG. 2 shows the results of immunoprecipitation of $^{35}$S-methionine labeled human $GAD_{65}$ and $GAD_{67}$ expressed from a baculovirus vector in Sf9 cells with MICAs, human IgG (control), the $GAD_{65}$-specific mouse monoclonal GAD6 and the $GAD_{67}$-specific rabbit antiserum K2. Immunoprecipitation of Sf9 cells infected with wild-type baculovirus is shown in parallel (lanes 15–21).

MICAs 1, 2, 3, 4, and 6 all recognized $GAD_{65}$, but not $GAD_{67}$, under native conditions. (See FIG. 2).

Figure 3:
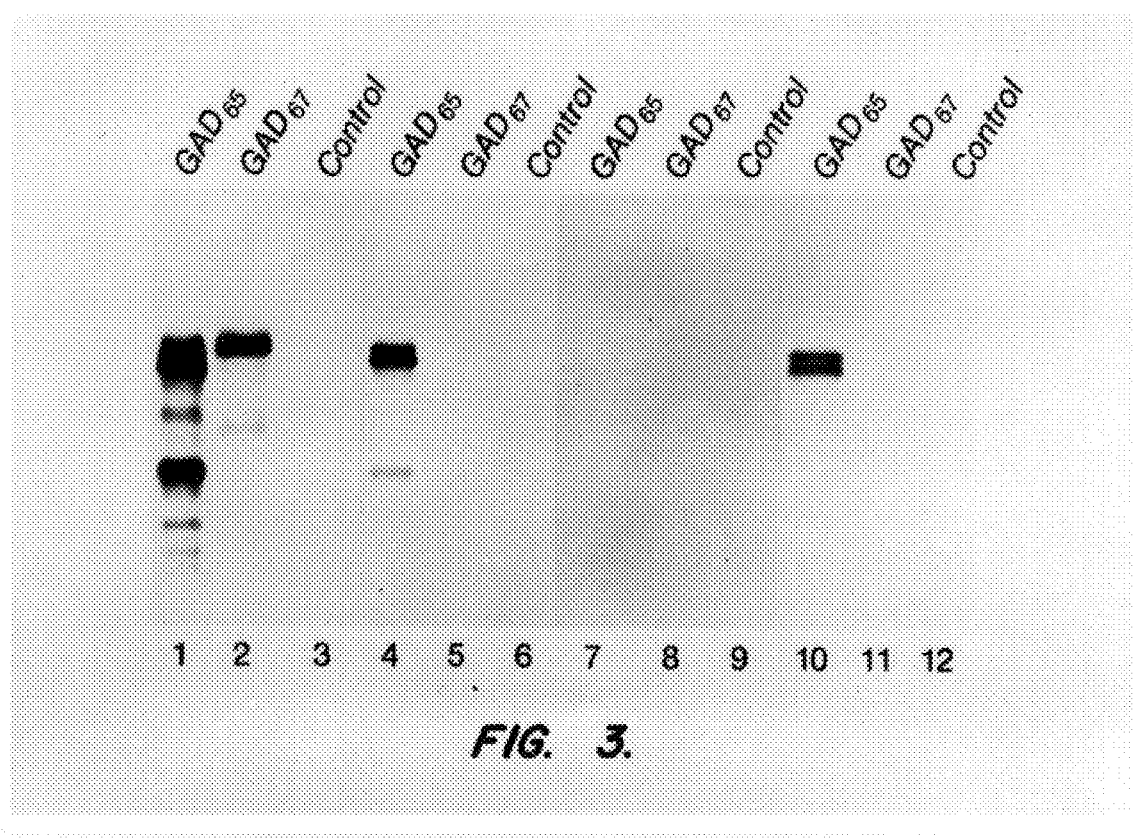
FIG. 3 shows a Western blot of human $GAD_{65}$ and $GAD_{67}$ expressed from a baculovirus vector in Sf9 cells along with Sf9 cells infected with wild-type baculovirus (control) using: 1266 antiserum that recognizes both $GAD_{65}$ and $GAD_{67}$ (lanes 1–3); GAD6 antiserum, which specifically recognizes $GAD_{65}$, (lanes 4–6), MICA 1 (lanes 7–9); and MICA 2 (lanes 10–12).

Example 4
Determination of Conformation Dependence of Epitopes Recognized by Insulin-Dependent Diabetes Mellitus Autoantibodies Conformation dependence was determined by testing the ability of MICAs 1–4 and 6 to bind to $GAD_{65}$ protein under denaturing conditions, as determined by Western blotting (see Christgau et al. (1992), supra, Baekkeskov et al. (1990), supra. Only MICA2 recognized denatured $GAD_{65}$ on Western blots (FIG. 3). Furthermore, serum of the type 1 diabetic patient from whom MICAs 1–6 were derived, weakly stained denatured $GAD_{65}$, but not $GAD_{67}$, on Western blots. The results show that MICAs 1, 3, 4 and 6 only recognize non-linear or conformational epitopes, whereas MICA2 recognizes a linear epitope specific for the $GAD_{65}$ molecule. Thus, the $GAD_{65}$ protein harbors linear, as well as nonlinear or conformational autoimrnune editopes, absent in the $GAD_{67}$ molecule.

Figure 4:
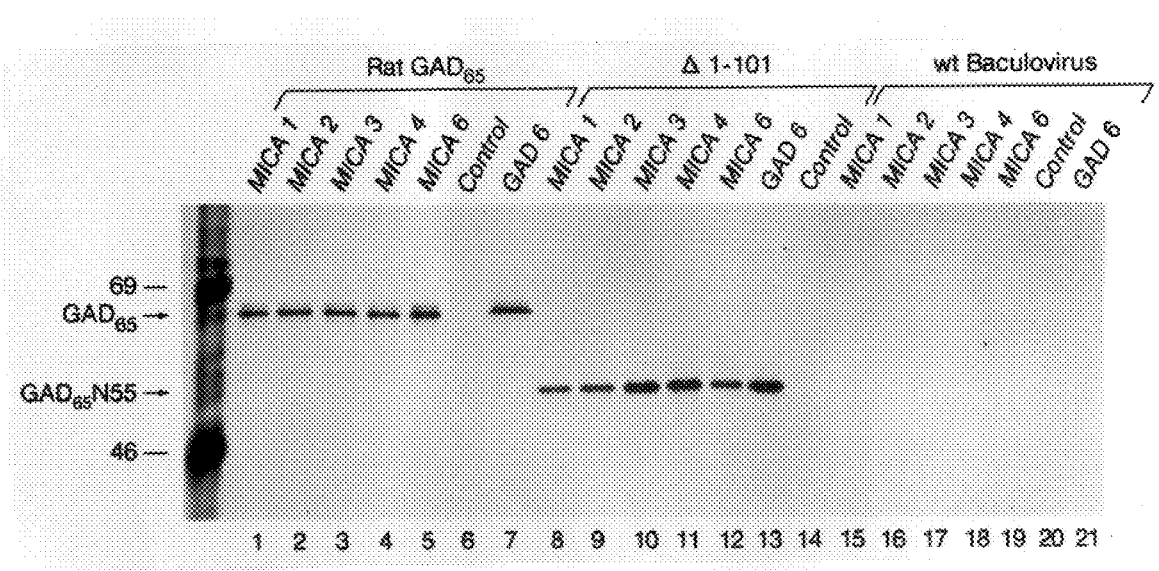
FIG. 4 shows the results of immunoprecipitation of $^{35}$S-methionine labeled wild-type rat $GAD_{65}$ and a truncated protein expressed from a baculovirus construct in Sf9 cells with MICAs, GAD6 (a mouse anti-$GAD_{65}$ monoclonal antibody), or human IgG (control). Immunoprecipitation of Sf9 cells infected with wild-type baculovirus is shown in parallel.
Figure 6A:
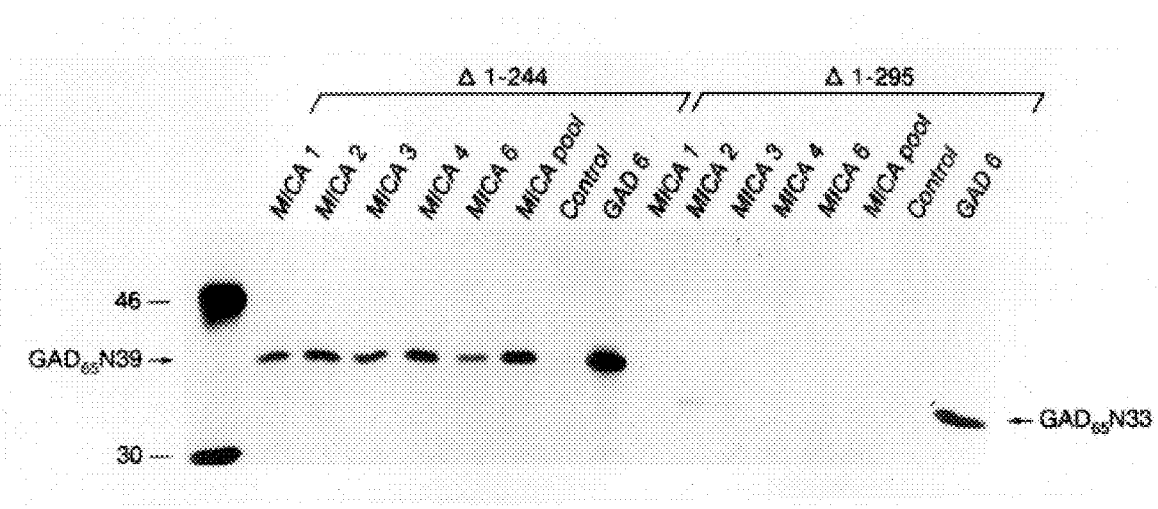
FIG. 6 shows the reactivity of MICAs with $GAD_{65}$ deletion mutants.
Figure 6B:
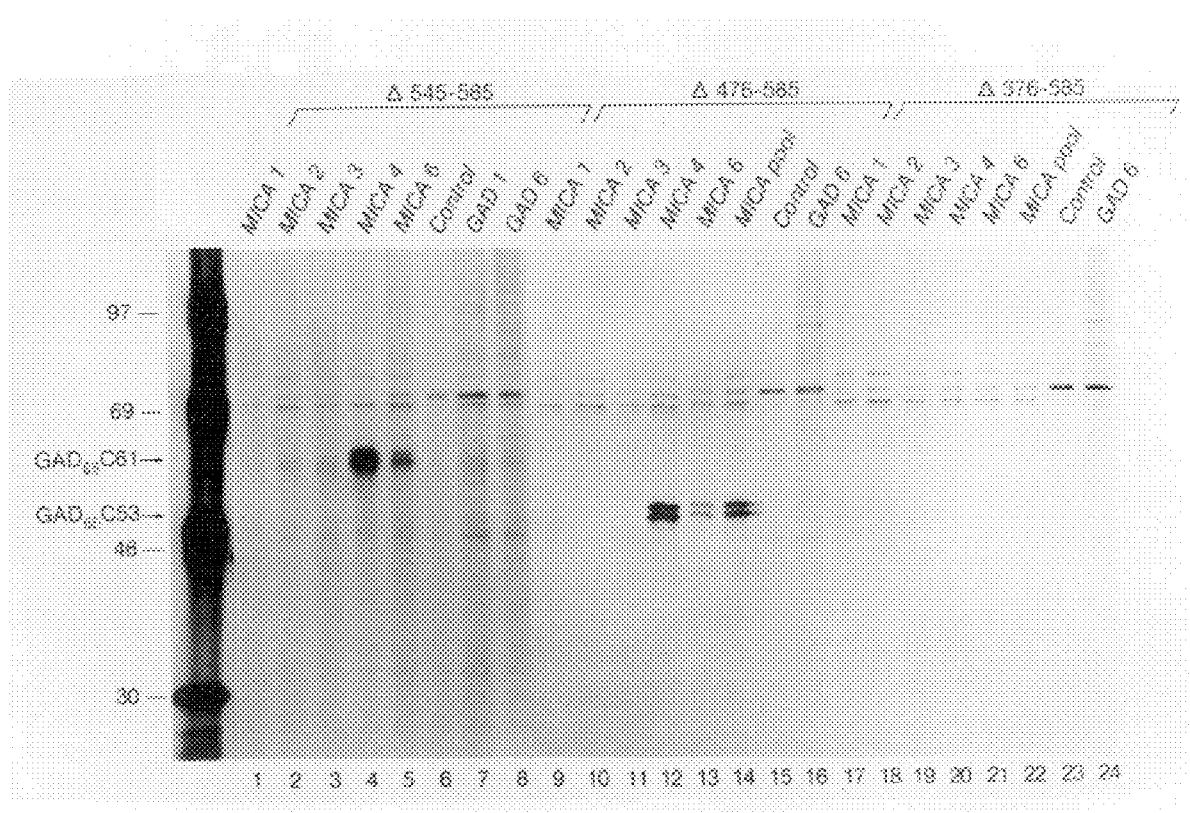

Example 5
Epitope Mapping of Insulin-Dependent Diabetes Mellitus Autoantibodies by Analysis of Deletion Mutants In immunoprecipitation experiments, all the MICAs recognized a deletion mutant lacking the first 101 amino acids (FIG. 4). To localize further the domains recognized by the MICAs, a number of N-terminal as well as C-terminal deletion mutants of rat $GAD_{65}$ expressed in COS-7 cells were tested for binding to MICAs. The size of the expressed $GAD_{65}$ fragments, their location in the amino acid sequence, and their reactivity with different MICAs are summarized in FIG. 6A. The N-terminal deletion mutant $GAD_{65}$N44, which lacks the first 194 amino acids, as well as the N-terminal deletion mutant $GAD_{65}$N39, which is missing additional 50 amino acids (Δ1–244), were recognized by all the monoclonals in immunoprecipitation experiments (FIGS. 6A and 6B). The N-terminal deletion mutant $GAD_{65}$N33, in which an additional 51 amino acids have been deleted from the N-terminus (Δ1–295) was, however, not recognized by MICAs 1, 4, and 6, and was either very weakly positive or negative with MICA3 and weakly positive with MICA2 in immunoprecipitation experiments (FIGS. 6A and 6B). MICA2 reacted equally well with this form on Western blots as with the full-length molecule. However, MICA2, was only weakly positive in immunoprecipitation experiments (FIGS. 6A and 6B), suggesting that the linear epitope recognized by this monoclonal antibody is sequestered in the folded truncated protein.

Figure 6C:
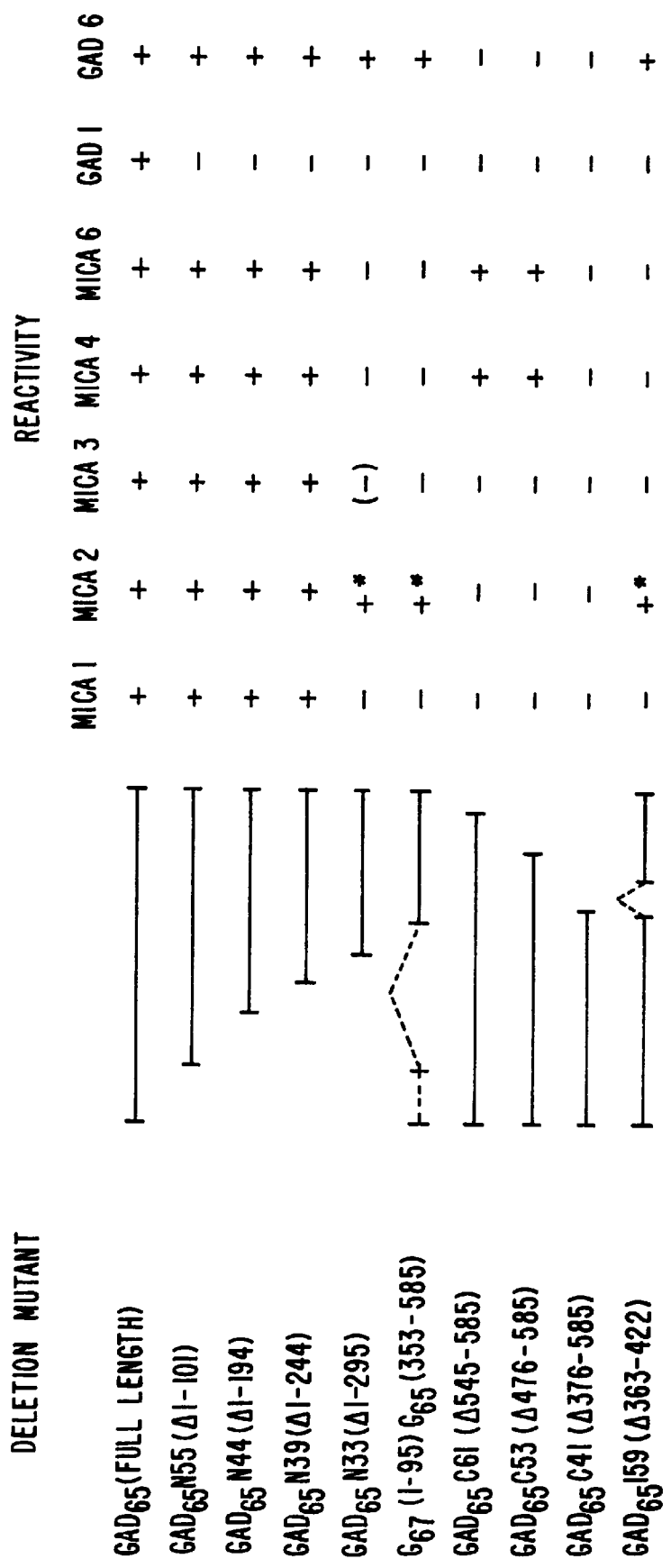

Analysis of C-terminal deletion mutants showed that the removal of 41 amino acids at the C-terminus abolished the binding of MICA1, MICA2 and MICA3 (FIG. 6A and 6C). However, MICA4 and MICA6 recognized both this mutant ($GAD_{65}$C61, Δ545–585) and the C-terminal deletion mutant $GAD_{65}$C53 (Δ476–585) which lacks an additional 69 amino acids at the C-terninus (FIGS. 6A and 6C). MICA4 showed a stronger binding to both mutants than MICA6. None of the monoclonals showed reactivity to the C-terminal deletion mutant $GAD_{65}$C41 (Δ376–585), which is missing an additional 100 amino acids at the C-terminus (FIG. 6A).

To analyze the effect of deletions in the internal part of the molecule, the binding of the MICAs to a deletion mutant, $GAD_{65}$I59, lacking amino acids 363–422 which harbor the pyridoxalphosphate binding site of the enzyme, was analyzed. None of the MICAs except MICA2 recognized this mutant in immunoprecipitation experiments. However although MICA2 reacted equally well with this mutant and the full-length molecule on Western blots, it bound only weakly in immunoprecipitation experiments (FIG. 6A) suggesting that the linear MICA2 epitope is only partially exposed under the native conditions of immunoprecipitation. The same reaction pattern was observed with a hybrid molecule containing amino acids 1–95 from $GAD_{67}$ linked to the last 233 amino acids of $GAD_{65}$ (FIG. 6A). It can be concluded that amino acids within the last 41 amino acids of the $GAD_{65}$ molecule are part of the linear epitope for MICA2. Amongst those 41 amino acids the last 16 are unlikely to play a role because they are identical to $GAD_{67}$ (see Erlander et al. (1991), Neuron. 7:91–100) and because excessive amounts of a peptide containing this sequence did not affect binding of any MICA to $GAD_{65}$. Amongst the 5 amino acids which differ between $GAD_{65}$ and $GAD_{67}$ in the remaining 25 amino acids, one is a conserved change. One or more of the remaining 4 amino acids are therefore likely to play a major role in the epitope of MICA2.

The analysis of deletion mutants indicates three principal recognition patterns of the MICAs. One, defined by MICAs 1 and 3, is dependent on the last 41 amino acids in the molecule. The second, defined by MICA4 and 6, is independent of these residues and confined to amino acids towards the center of the molecule. The third, defined by MICA2, is dependent on the last 41 amino acids in the molecule, but is independent of other amino acids.

$GAD_{67}$ and $GAD_{65}$ are highly diverse in the first 95 amino acids but share significant (approx. 75%) homology in the rest of the molecule. See Erlander et al. (1991), supra. However, surprisingly, none of the $GAD_{65}$-specific epitopes recognized by the MICAs was localized in the first 244 amino acids at the N-terminus. Thus, the epitopes of the MICAs are concentrated in areas of the molecule that are significantly distant from the N-terminal membrane-anchoring domain. The last 110 amino acids at the C-terminus do not contribute to the MICA 4 and 6 epitope (s), which span(s) residues in the middle of the molecule. In contrast, deletion of 41 amino acids at the C-terminus abolishes the MICAs 1 and 3 epitope. Furthermore, deletion of amino acids 245–295 abolishes all the conformational changes in the C-terminal region, as suggested by the weak binding of MICA2 to this mutant, whereas deletion of amino acids 1–41 and 42–110 in the C-terminus does not seem to affect the middle region of the $GAD_{65}$ molecule where the MICAs 4 and 6 epitopes remain intact. Finally, MICA3 did bind weakly to the $GAD_{65}N33$ mutant, whereas no binding to the C-terminal deletion mutants was detected. Thus deletion of amino acids 244–295 likely affects the conformation of the C-terminal region, whereas deletion of the C-terminal amino acids appears to affect the MICA 1 and 3 epitopes directly. A significant part of the linear MICA2 epitope is localized between amino acids 545 and 569, i.e., close to the C-terminus. Example 6
Epitope Mapping of $GAD_{65}$ Autoantibodies by Protein Footprinting The similarities and differences in epitope recognition by the MICAs were analyzed by protein footprinting (see Sheshberadaran & Payne (1988), *Proc. Natl. Acad. Sci.* 35:1–5) (incorporated by reference in its entirety for all purposes), using 500 µl MICA supernatant or 10 µl GAD6 or GAD1 ascites respectively. Immune complexes were isolated by binding to protein-A-sepharose and washed. To stabilize the immune complexes, anti-human IgG antibody (H+L-specific, F(ab)$_2$-fragments, Jackson) was incubated with the antigen antibody PAS complex for 45 minutes at 4° C. before incubation with proteases. Incubations with proteases were for 30 minutes on ice (chymotrypsin and trypsin) or 1 hour at 37° C. (chymotrypsin). Protease treatment was stopped by washing the PAS-bound complexes in IMP-buffer, and followed by SDS-PAGE analysis and fluorography. Immunocomplexes of $GAD_{65}$, bound to individual MICAs and stabilized by binding to a secondary antibody, were digested with trypsin and chymotrypsin. The fragments protected from degradation by the MICAs were then analyzed by SDS-PAGE.

Figure 5:
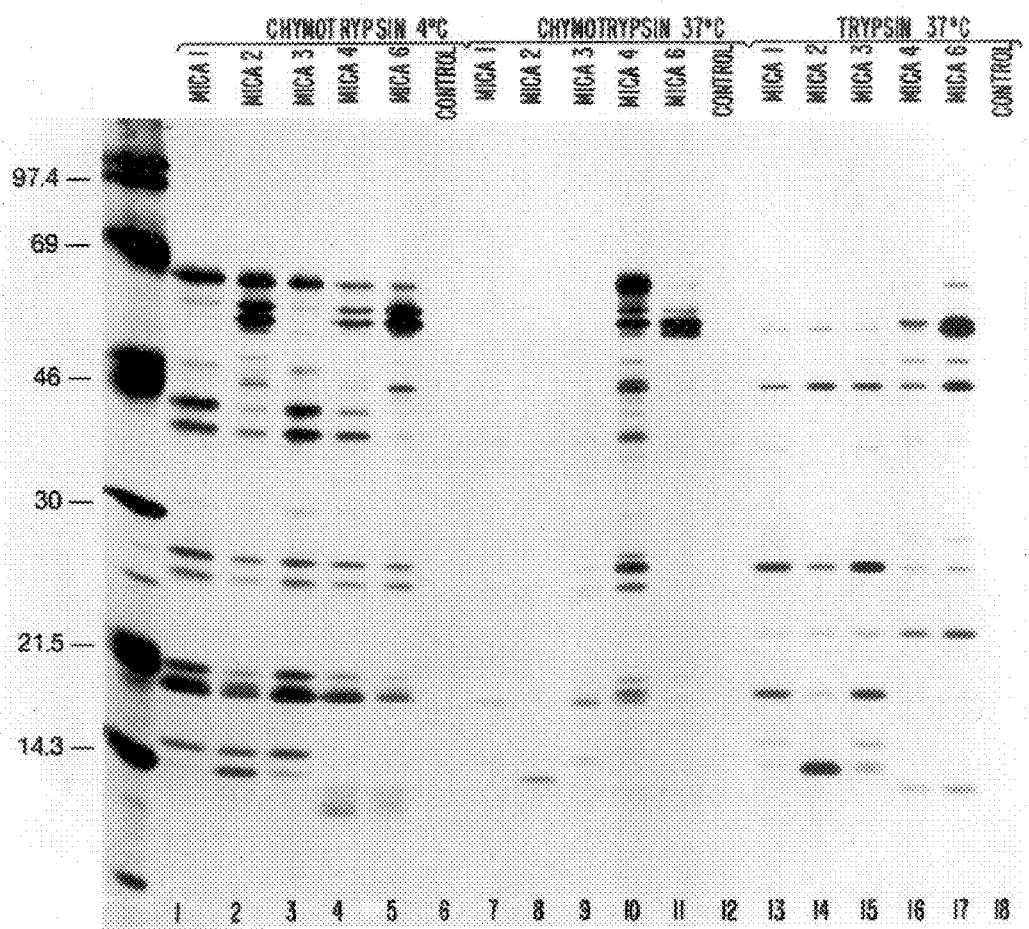
FIG. 5 shows protein footprinting of immuno-complexes between the MICAs or human IgG (control) and $^{35}$S-methionine-labeled human $GAD_{65}$ from Sf9 cells.

FIG. 5 shows two major distinct footprinting patterns which distinguish MICA 1, 2 and 3 from MICA 4 and 6. Within the first group MICA 1 and 3 displayed identical patterns that were similar yet distinct from that of MICA2. Furthermore, in the second group MICA4 and MICA6 displayed only minor differences (FIG. 5).

Both MICA4 and MICA6 protected the full-length $GAD_{65}$ molecule and a 55 kDa fragment lacking the N-terminus (see Christgau et al. (1992), supra, more effectively than did MICAs 1, 2 and 3. Thus, in contrast to MICAs 4 and 6, no full-length $GAD_{65}$ or 55 kDa fragment was detected in immunocomplexes with MICAs 1, 2 and 3 following prolonged chymotrypsin incubation. (FIG. 5, compare lanes 10 and 11 with lanes 7 and 9). These results suggest that MICA4 and MICA6 bind areas of the molecule closer to the N-terminus and therefore protect this part of the molecule better than MICAs 1, 2, and 3.

While MICAs 1, 3, 4 and 6 still displayed a complex footprinting pattern following prolonged incubations with chymotrypsin (FIG. 5, lanes 7–12), only 1 band of approximately 14 kDa was protected by MICA2 under those conditions (FIG. 5, lane 8).

In sum, the complex footprinting patterns of MICAs 1, 3, 4 and 6 are consistent with a nonlinear epitope recognition, whereas the 14 kDa single fragment protected by MICA2 is consistent with a linear epitope recognition by this monoclonal antibody. Furthermore, the footprinting results suggest that MICAs 4 and 6 recognize areas more toward the N-terminus than MICAs 1, 2, and 3.

Example 7
Use of $GAD_{65}$ Fragments for Diagnosis of Sera from Type 1 Diabetic Patients Sera from nine young newly-diagnosed type 1 diabetic patients (D1–9, FIG. 7) age 4½ to 26 years (6F, 3M), and 1 prediabetic individual (PI, female, age 11 years) sampled 32 months before clinical onset of disease, were analyzed for their binding to the N-terminal and C-terminal deletion mutants. Sera from type 1 diabetic patients were obtained from Dr. H. J. Aanstoot (University of Rotterdam, The Netherlands) or described earlier (see Baekkeskov et al. (1987), *J. Clin. Invest.* 79:926–934) (incorporated by reference in its entirety for all purposes).

In addition, sera from the patient from whom the MICAs were derived from (D10) and from another individual (male 24 yrs), positive for islet cell cytoplasmic autoantibodies, but having no clinical symptoms of type 1 diabetes (P2), were analyzed in parallel (FIG. 7). All eleven new sera recognized the N-terminal deletion mutant $GAD_{65}N44$ (Δ1–194) (FIG. 7) equally well as the full-length molecule. Deletion of 244 N-terminal amino acids ($GAD_{65}N39$) resulted in a slightly decreased reactivity with some of the sera (FIG. 7), whereas further deletion of 51 amino acids ($GAD_{65}N33$) abolished recognition by all of the sera. The sera proved distinguishable in the analysis of the mutant lacking 41 amino acids at the C-terminus ($GAD_{65}C61$). Four sera including the serum from the prediabetic individual (PI), sampled 32 months before clinical onset of disease, as well as sera from three newly diagnosed patients (D3, female 11 years, D4, male 4.5 years, and D5, male 26 years), all of which were strongly positive for $GAD_{65}$ antibodies, either showed very weak or no reactivity with the $GAD_{65}C61$ mutant (FIG. 7). The remainder of the sera were still strongly positive for this truncated protein (FIG. 7). In sum, deletion of ⅓ of the $GAD_{65}$ molecule form the N-terminus did not result in a detectable decrease in immunoreactivity with the diabetic sera, whereas deletion of 41 amino acids from the C-terminus effectively abolished the epitopes recognized by some of the patient sera. None of the 11 patient sera recognized $GAD_{65}$ on Western blots and thus did not contain autoantibodies with a linear epitope recognition, such as MICA2.

The relative frequencies with which the three different classes of diabetes-mellitus autoantibodies occur in different sera samples may be related to the time at which they are produced. In autoimmune diseases, both humoral and cellular autoimmunity are often directed to a single dominant epitope in the early phases but may spread to other regions in the autoantigen with increased duration of autoimmune responses (see McNeilage et al. (1990), *J. Immunol.* 145:3829–3835; St. Clar et al. (1990), *J. Clin. Invest.* 85:515; Lehmann et al. (1992), *Nature* 358:155–157) (each of which is incorporated by reference in its entirety for all purposes). $GAD_{65}$ autoantibodies have been detected during early phases of pancreatic β-cell destruction, which is often several years before the majority of the β-cells have vanished and the clinical symptoms develop (see Baekkeskov et al. (1987), supra, Atkinson et al. (1990), *Lancet*

335:1357–1360) (which is incorporated by reference in its entirety for all purposes). These observations suggest that the primary autoimmune response may be limited to autoantibodies against a single epitope, with more diverse autoantibodies developing subsequently during the primary autoimmune response. It is therefore likely that the $GAD_{65}$ epitopes defined by the MICAs represent both early and late humoral responses. The epitope defined by MICAs 1 and 3, which was recognized by all sera tested, is likely indicative of an early humoral response. The epitope defined by MICAs 4 and 6, which was recognized by some, but not all, sera tested, likely represents an intermediate humoral response. The epitope defined by MICA2, which was only recognized by sera, from the patient from whom the MICA was derived, likely represents a late humoral response. The progressive temporal responses proposed for the different classes of epitopes can be confirmed by monitoring serum samples from prediabetic individuals over a period of time.

Example 8
Epitope Mapping of Stiff Man Syndrome Autoantibodies

Experiments have been performed to localize epitopes recognized by sera from SMS patients on the $GAD_{65}$ molecule. N-terminal $GAD_{65}$ deletion mutants were constructed in which the first 69–70 or the first 101 amino acids were deleted. These fragments were tested for binding to autoantibodies in sera from SMS patients under denaturing conditions. FIG. 8 shows staining of Western blots of intact $GAD_{67}$, intact $GAD_{65}$, a 57 kDa tryptic fragment of $GAD_{65}$, lacking the first 69–70 amino acids, and a 55 kDa deletion mutant of $GAD_{65}$ lacking the first 101 amino acids with i) a typical SMS serum, which recognizes $GAD_{65}$ but not $GAD_{67}$, shows a weaker staining with the 57 kDa fragment than the full-length protein, and shows no reactivity with the 55 kDa deletion mutant, ii) a control rabbit polyclonal rabbit sera, which stains all fragments.

FIG. 8 shows that the reactivity of SMS sera with the $GAD_{65}$ protein drops significantly in the $GAD_{65}$ fragment lacking the first 69–70 amino acids, indicating that a linear epitope is localized within these residues. The complete loss of reactivity in the $\Delta101$ $GAD_{65}$ fragment indicates that a second epitope is located between amino acid 69 or 70 and amino acid 101. Of 26 samples of SMS sera analyzed, 22 showed the above results.

The two linear epitopes identified by Western blotting have been further localized by competitive binding experiments using artificial $GAD_{65}$ peptides. It has been found that peptides comprising $GAD_{65}$ amino acids 1–20 or 70–101 effectively compete with SMS sera for binding to $GAD_{65}$. The results localize one epitope to amino acids 1–20, and another epitope to amino acid 70–101.

The clear difference in epitope recognition between autoantibodies from IDDM and stiff man syndrome patients suggests that the humoral autoimmunity to $GAD_{65}$ is probably related to the different pathogenic mechanisms through which stiff man syndrome or IDDM arises.

Example 9
Localization of the $GAD_{65}$ N-Terminal Domain that Confers Insolubility on the Intact Protein As previously discussed, the N-terminal domain of $GAD_{65}$ contains lipid modifications that render the intact protein insoluble in aqueous solvents. This Example localizes the amino acid sites at which modification occurs, and which must be removed to generate a soluble $GAD_{65}$ fragment.

To test whether cysteine residues at positions 30 and 45 are sites of palmitoylation, $GAD_{65}$ mutant polypeptides were constructed by site-directed mutagenesis in which one or both of these residues were replaced with alanine residues. The single mutants were termed 30A and 45A, and the double mutant was termed 30/45A. Vectors containing these three GAD mutants, wild-type $GAD_{65}$ or a $GAD_{65}$ $\Delta101$ mutant were transiently expressed in COS cells in media containing [$^3$H]-palmitic acid or [$^{35}$S]-methionine. $GAD_{65}$ polypeptides were immunoprecipitated and analyzed by SDS PAGE. FIG. 9 compares incorporation of label in wild-type; the 30A mutant, the 45a mutant, the $\Delta1$–101 mutant, and the 30/45A mutant. The figure shows that the 30/45A double mutant, but not the 30A or 45A single mutants, has lost the ability to become palmitoylated. The $\Delta101$ mutant has also lost the ability to become palmitoylated.

Although the above analysis identifies amino acids 30 and 45 as the sites of palmitoylation, other N-terminal amino acids may be the subject of other lipid modifications. This possibility was tested by constructing a series of deletion mutants of the $GAD_{65}$ 30/45A fragment, in which increasing amounts of N-terminal sequence were deleted. The fragments were inserted into expression vectors and transformed into COS cells. Total cellular protein of COS cells expressing $GAD_{65}$ or an U-terminal deletion mutant was extracted with Hepes buffer plus 1% TX-114, and partitioned into aqueous (A) and detergent (D) phases in a TX-114 partition assay. The fractions were analyzed by SDS page, and $GAD_{65}$ polypeptides detected by Western blotting using sera against a $GAD_{65}$ C-terminal peptide as the probe. FIG. 10 shows that for wild-type $GAD_{65}$ and the 30/45A $\Delta1$–8, 30/45A $\Delta1$–15 and 30/45A $\Delta1$–23 deletion mutants, the $GAD_{65}$ fragment appears in both aqueous and detergent phases. However, for the 30/45A $\Delta1$–31 and 30/45A $\Delta1$–38 mutants, the $GAD_{65}$ fragment appears exclusively in the aqueous phase. Comparison of the amino acids present in the hydrophobic and hydrophilic polypeptides indicates that acids 24–31 confer hydrophobicity of $GAD_{65}$ polypeptides.

These results have been confirmed by immunofluorescence analysis of intact cell expressing wild-type $GAD_{65}$ or a 30/45A $\Delta1$–38 deletion mutant thereof. Whereas the wild-type $GAD_{65}$ protein is found concentrated in perinuclear membranous structures consistent with membrane anchoring, the location of the N-terminal deletion mutant is cystosolic.

It is concluded that a soluble $GAD_{65}$ fragment can be produced by deletion of amino acids 24–31 and, preferably, mutation of amino acid 45. Of course, more substantial N-terminal deletions that encompass these changes are also effective, for example, deletion of amino acids 1–45. A soluble $GAD_{65}$ fragment would also be produced by synthesizing the fragment under conditions, e.g., in vitro translation, under which post-translation modifications do not occur.

Although the foregoing invention has been described in detail for purposes of clarity of understanding, it will be obvious that certain modifications may be practiced within the scope of the appended claims. All publications and patent documents cited above are hereby incorporated by reference in their entirety for all purposes to the same extent as if each were so individually denoted.

What is claimed is:

1. A GAD65 polypeptide comprising amino acids 70–101 of GAD65 and having a solubility of at least 50 µ/ml in an aqueous solvent, wherein the polypeptide is substantially free of N-terminal amino acids that limit solubility by deletion or substitution of said N-terminal amino acids relative to a natural GAD65 polypeptide.

2. The GAD65 polypeptide of claim 1, further comprising amino acids 245–585.

3. The GAD65 polypeptide of claim 1, wherein the fragment lacks palmitoylation a t amino acids 31 and 45.

4. The GAD65 polypeptide of claim 1, wherein the fragment is substantially free of N-terminal amino acids 24 to 31.

5. The GAD65 polypeptide of claim 1, wherein the fragment is substantially free of N-terminal amino acids 24–31 and 45.

6. The GAD65 polypeptide of claim 1, further comprising a contiguous sequence from about amino acids 245 to 585 and having three different epitopes specifically reactive with three different $GAD_{65}$ autoantibodies.

7. A GAD65 polypeptide having a solubility of at least 50 µg/ml in an aqueous solvent comprising amino acids 1–20 and 245–585 of GAD65, wherein the polypeptide is substantially free of N-terminal amino acids that limit solubility by deletion or substitution of said N-terminal amino acids relative to a natural GAD65 polypeptide.

8. A method of producing a GAD65 polypeptide having a solubility of at least 50 µg/ml in an aqueous solvent, comprising culturing a eucaryotic cell expressing a nucleic acid encoding the GAD65 polypeptide in the presence of an inhibitor of lipid attachment to the polypeptide;

isolating the GAD65 polypeptide from the cell culture.

* * * * *